(12) United States Patent
Brown et al.

(10) Patent No.: US 9,119,811 B2
(45) Date of Patent: Sep. 1, 2015

(54) FLUOROCARBON-LINKED PEPTIDE FORMULATION

(75) Inventors: Carlton Bradley Brown, Santa Cruz la Laguna (GT); Bertrand Victor Gilbert Georges, Stevenage (GB); Jean Francois Thaburet, London (GB)

(73) Assignee: Vaxin UK Limited, London (GB)

( * ) Notice: Subject to any disclaimer, the term of this patent is extended or adjusted under 35 U.S.C. 154(b) by 0 days.

(21) Appl. No.: 13/977,265

(22) PCT Filed: Dec. 30, 2011

(86) PCT No.: PCT/GB2011/001781
§ 371 (c)(1),
(2), (4) Date: Aug. 15, 2013

(87) PCT Pub. No.: WO2012/090002
PCT Pub. Date: Jul. 5, 2012

(65) Prior Publication Data
US 2013/0330382 A1 Dec. 12, 2013

(30) Foreign Application Priority Data
Dec. 31, 2010 (GB) .................................. 1022147.1

(51) Int. Cl.
| | | |
|---|---|---|
| A61K 9/00 | (2006.01) |
| A61K 39/12 | (2006.01) |
| A61K 38/00 | (2006.01) |
| C07K 5/00 | (2006.01) |
| C07K 7/00 | (2006.01) |
| C07K 16/00 | (2006.01) |
| C07K 17/00 | (2006.01) |
| C07K 1/00 | (2006.01) |
| A61K 39/145 | (2006.01) |
| A61K 39/00 | (2006.01) |
| A61K 47/48 | (2006.01) |
| A61K 39/385 | (2006.01) |

(52) U.S. Cl.
CPC .............. *A61K 39/145* (2013.01); *A61K 39/00* (2013.01); *A61K 39/385* (2013.01); *A61K 47/4833* (2013.01); *A61K 2039/60* (2013.01); *A61K 2039/6093* (2013.01); *C12N 2760/16034* (2013.01); *C12N 2760/16134* (2013.01)

(58) Field of Classification Search
CPC .............. A61K 39/145; A61K 39/385; A61K 47/4833; A61K 39/00; A61K 2039/60; A61K 2039/6013; C12N 2760/16134; C12N 2760/16034
See application file for complete search history.

(56) References Cited

U.S. PATENT DOCUMENTS

| 7,687,455 | B2 | 3/2010 | Bonnet et al. | |
| 8,110,540 | B2 | 2/2012 | Bonnet et al. | |
| 8,110,541 | B2 | 2/2012 | Bonnet et al. | |
| 8,129,333 | B2 | 3/2012 | Bonnet et al. | |
| 8,642,531 | B2 | 2/2014 | Bonnet et al. | |
| 2008/0145383 | A1* | 6/2008 | Zauner et al. | 424/208.1 |
| 2009/0191233 | A1* | 7/2009 | Bonnet et al. | 424/186.1 |
| 2012/0315293 | A1 | 12/2012 | Bonnet et al. | |

FOREIGN PATENT DOCUMENTS

| EP | 0 327 070 A | 8/1989 |
| WO | WO-2005/094891 | 10/2005 |
| WO | WO-2005/099752 | 10/2005 |
| WO | WO-2009/027688 | 3/2009 |
| WO | WO 2009027688 A1 * | 3/2009 |
| WO | WO-2012/090002 | 7/2012 |

OTHER PUBLICATIONS

Anonymous. "Peptide Solubility" Sigma Aldrich. <http://www.sigmaaldrich.com/life-science/custom-oligos/custom-peptides/learning-center/peptide-solubility.html> Accessed online Sep. 23, 2014, originally published Dec. 4, 2008.*
Beebe et al. (2008) "Formulation and characterization of a ten-peptide single vial vaccine, EP-2101, designed to induce cytotoxic T-lymphocyte responses for cancer immunotherapy" Human Vaccines, 4(3):210-218.
Bonnet et al. (2005) "Effect of Glycoamphiphiles on the Solubilization and Dendritic Cell Uptake of a Lipopeptide: A Preliminary Study" Mol. Pharm., 2(5):420-427.
Deres et al. (1989) "In vivo priming of virus-specific cytotoxic T lymphocytes with synthetic lipopeptide vaccine" Nature, 342:561-564.
Do et al. (2008) "Broad T cell immunity to the LcrV virulence protein is induced by targeted delivery to DEC-205/CD205-positive mouse dendritic cells" Eur. J. Immunol., 38:20-29.
Europharmatoday website (http://www.europharmatoday.com/2009/08/startup-profile-immune-targeting-systems-ltd-synthetic-vaccines-against-mutating-viruses.html, accessed May 11, 2011).
Fayolle et al. (2004) "*Bordetella pertussis* adenylate cyclase delivers chemically coupled CD8+ T-cell epitopes to dendritic cells and elicits CTL in vivo" Vaccine, 23:604-614.
Felix et al. (1995) "Pegylated peptides. IV. Enhanced biological activity of site-directed pegylated GRF analogs" Int. J. Pept. Protein Res., 46:253-264.
International Search Report for PCT/GB11/001781 (Immune Targeting Systems), mailed on Apr. 10, 2012 (4 pages).

(Continued)

*Primary Examiner* — James H Alstrum Acevedo
*Assistant Examiner* — Zachary J Miknis
(74) *Attorney, Agent, or Firm* — Goodwin Procter LLP

(57) ABSTRACT

The invention provides an aqueous acidic formulation suitable for use as in the preparation of a pharmaceutically acceptable fluorocarbon-linked peptide formulation, which aqueous formulation comprises a first fluorocarbon-linked peptide, wherein: the peptide linked to the fluorocarbon is at least 20 amino acid residues long, comprises at least 50% hydrophobic amino acid residues and has an isoelectric point greater than or equal to 7; and the fluorocarbon-linked peptide is present in micelles.

13 Claims, 15 Drawing Sheets

(56) References Cited

OTHER PUBLICATIONS

Jones et al. (2005) "Characterisation of cell-penetrating peptide-mediated peptide delivery" Br. J. Pharmacol., 145:1093-1102.

Krafft et al. (2009) "Chemistry, Physical Chemistry, and Uses of Molecular Fluorocarbon-Hydrocarbon Diblocks, Triblocks, and Related Compounds—Unique "Apolar" Components for Self-Assembled Colloid and Interface Engineering" Chem. Rev., 109:1714-1792.

Ozer et al. (1999) "Synthesis of perfluoroalkyltated beta-alanine and some peptide derivatives: an access to original surfactants" Amino Acids, 16:381-389.

Perrie et al.(2007) "Recent developments in particulate-based vaccines" Recent Pat. Drug Deliv. Formul., 1(2):117-129.

Riess et al. (1991) "Highly effective surfactants with low hemolytic activity" Advanced Materials, 3(5):249-251.

Samad et al. (2007) "Liposomal drug delivery systems: an update review" Current Drug Deliv., 4:297-305.

"Solvent Systems and Their Selection in Pharmaceutics and Biopharmaceutics," Springer (2007) Augustijns, P. and Brewster, M., eds. "Chapter I. Principles of Solubility," Gong et al., pp. 1-27.

Written Opinion for PCT/GB11/001781 (Immune Targeting Systems), dated on Apr. 10, 2012 (7 pages).

* cited by examiner

Figure 3

| FCP | 80% v/v Acetic acid | | 80% v/v propan-2-ol | | 80% v/v tert-butanol | | 80% v/v DMSO | | 80% v/v Acetone | |
|---|---|---|---|---|---|---|---|---|---|---|
| | Clarity | Foam / particulates | Clarity | Particulates | Clarity | Foam / particulates | Clarity | Foam / particulates | Clarity | Particulates |
| FCP1 | +++ | - / - | + | ++ | + | - / ++ | + | +++ / ++ | + | ++ |
| FCP2 | +++ | - / - | + | ++ | + | - / ++ | + | ++ / ++ | + | ++ |
| FCP3 | +++ | - / - | + | ++ | + | - / ++ | + | ++ / ++ | + | ++ |
| FCP4 | +++ | - / - | - | ++ | +++ | - / ++ | + | ++ / ++ | +++ | ++ |
| FCP5 | +++ | - / - | + | ++ | + | - / ++ | + | ++ / ++ | + | ++ |
| FCP6 | +++ | - / - | - | ++ | + | - / ++ | + | ++ / ++* | - | ++ |
| FCP7 | +++ | - / - | - | ++ | + | - / ++ | + | ++ / ++ | + | ++ |
| FCP8 | +++ | - / - | - | ++ | + | - / ++ | + | + / ++ | + | ++ |
| FCP9 | +++ | - / - | - | ++ | + | - / ++ | + | ++ / ++ | + | ++ |
| FCP10 | +++ | - / - | - | ++ | + | - / ++ | + | ++ / ++ | + | ++ |
| FCP11 | +++ | - / - | - | ++ | + | - / ++ | + | ++ / ++ | + | ++ |
| FCP12 | +++ | - / - | - | ++ | + | - / ++ | + | + / ++ | + | ++ |

Figure 4

| FCP | 80% v/v Acetic acid | | 80% v/v propan-2-ol | | 80% v/v tert-butanol | | 80% v/v DMSO | | 80% v/v Acetone | |
|---|---|---|---|---|---|---|---|---|---|---|
| | Clarity | Foam / particulates | Clarity | Foam / particulates | Clarity | Foam / particulates | Clarity | Foam / particulates | Clarity | Foam / particulates |
| FCP1 | +++ | - / - | +++ | - / - | +++ | ++ / - | +++ | - / - | ++ | ++ / - |
| FCP2 | +++ | - / - | +++ | - / - | +++ | ++ / - | +++ | ++ / - | +++ | ++ / - |
| FCP3 | +++ | - / - | +++ | - / - | +++ | ++ / - | +++ | ++ / - | +++ | ++ / - |
| FCP4 | +++ | - / - | +++ | ++ / ++ | +++ | + / ++ | + | ++ / ++ | +++ | - / ++ |
| FCP5 | +++ | - / - | - | - / ++ | +++ | + / ++ | +++ | ++ / ++ | + | - / ++ |
| FCP6 | +++ | - / - | + | ++ / - | + | + / + | + | - / ++ | +++ | - / - |
| FCP7 | +++ | - / - | +++ | ++ / - | +++ | - / - | +++ | ++ / ++ | + | - / ++ |
| FCP8 | +++ | - / - | - | ++ / - | + | ++ / ++ | + | ++ / - | + | ++ / ++ |
| FCP9 | +++ | - / - | +++ | - / - | +++ | ++ / + | +++ | ++ / - | +++ | ++ / - |
| FCP10 | +++ | - / - | +++ | - / - | + | ++ / + | +++ | ++ / - | +++ | ++ / - |
| FCP11 | +++ | - / - | - | ++ / - | + | ++ / ++ | + | +++ / - | + | ++ / - |
| FCP12 | +++ | - / - | - | ++ / - | + | ++ / ++ | + | ++ / - | + | ++ / ++ |
| Mix 1 | +++ | - / - | ++ | - / ++ | + | - / ++ | + | - / ++ | + | ++ / ++ |
| Mix 2 | +++ | - / - | ++ | - / ++ | + | - / ++ | + | - / ++ | + | ++ / ++ |

FIG. 7A

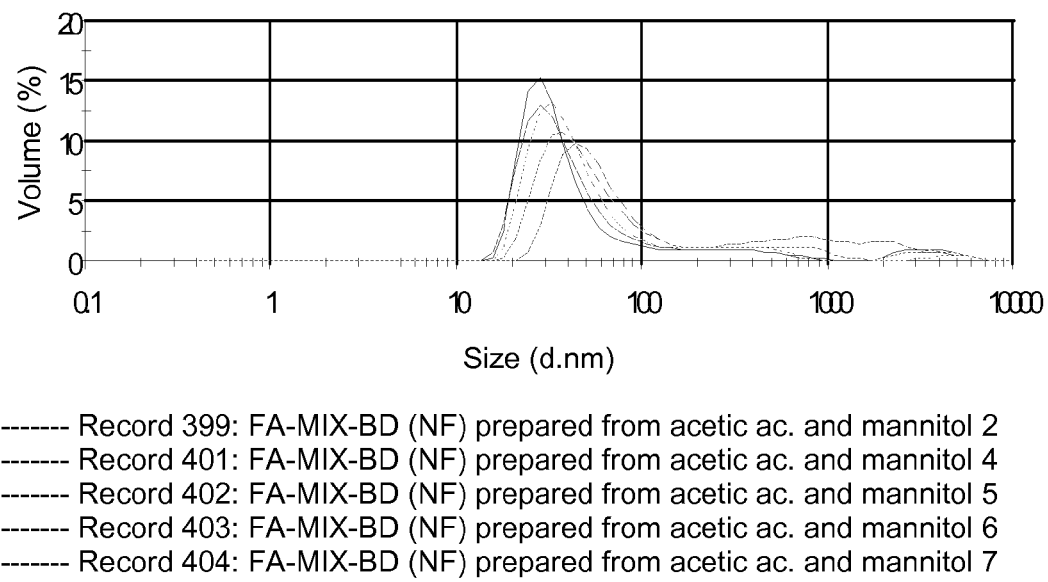

--------- Record 399: FA-MIX-BD (NF) prepared from acetic ac. and mannitol 2
--------- Record 401: FA-MIX-BD (NF) prepared from acetic ac. and mannitol 4
--------- Record 402: FA-MIX-BD (NF) prepared from acetic ac. and mannitol 5
--------- Record 403: FA-MIX-BD (NF) prepared from acetic ac. and mannitol 6
--------- Record 404: FA-MIX-BD (NF) prepared from acetic ac. and mannitol 7

FIG. 7B

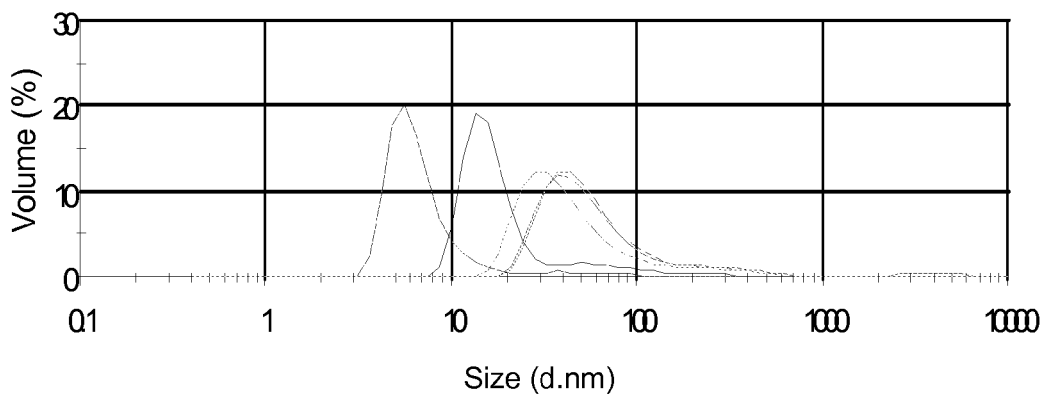

--------- Record 393: FA-MIX-BD (NF) prepared from acetic ac. and mannitol 3
--------- Record 394: FA-MIX-BD (NF) prepared from acetic ac. and mannitol 4
--------- Record 395: FA-MIX-BD (NF) prepared from acetic ac. and mannitol 5
--------- Record 396: FA-MIX-BD (NF) prepared from acetic ac. and mannitol 6
--------- Record 397: FA-MIX-BD (NF) prepared from acetic ac. and mannitol 7

FLUOROCARBON-LINKED PEPTIDE FORMULATION

CROSS-REFERENCE TO RELATED APPLICATIONS

This application is the U.S. National Stage of International Application No. PCT/GB2011/001781, filed Dec. 30, 2011, which claims priority to United Kingdom Patent Application No. 1022147.1, filed Dec. 31, 2010, the complete disclosures of each of which are incorporated by reference herein.

FIELD OF THE INVENTION

The invention relates to pharmaceutically acceptable formulations comprising fluorocarbon-linked peptides, formulations useful in the preparation of such pharmaceutically acceptable formulations, a method of preparing such formulations and the use of such formulations as vaccines and immunotherapeutics.

BACKGROUND TO THE INVENTION

Synthetic peptide antigens are of interest for use in vaccines to prevent infectious diseases (such as viral, bacterial, parasitic and fungal infections). Synthetic peptide antigens are also of interest in the field of immunotherapeutics, including the treatment of infection, the stimulation of immunity to cancer cells, the down-regulation of polypeptide hormones and the control of inappropriate immune responses such as anaphylaxis and allergy.

One difficulty in the practical use of peptide-based vaccines and immunotherapies is ensuring the induction of an immune response by efficient delivery of the peptide antigens to an antigen presenting cell. Without such targeting, unfeasible amounts of the peptide may be required, which would not only be uneconomical to manufacture but could also lead to toxicity issues.

Enhancement of peptide delivery may be achieved through specialised delivery vehicles, such as particulate-based structures enabling sustained release. In addition, peptide derivatives or modified peptides comprising the peptide of interest covalently linked to a delivery-enhancing agent have been developed to improve the bio-availability and presentation of the peptide to specific target cells and receptors.

One particular class of peptides modified to improve delivery to antigen presenting cells are constructed through the covalent attachment of a fluorocarbon chain to either the peptide N- or C-terminus, or at any position in between, to create a fluorocarbon-linked peptide (FCP). Examples of fluorocarbon-linked peptides are given in WO2005/099752 and WO2009/027688 and the advantages afforded by the fluorocarbon attachment in the enhancement of immune responses to the peptide are provided therein.

It will be understood by vaccine designers that more than one peptide may be required to provide a broader prophylactic or immunotherapeutic effect. Such multi-component products are desirable since they are likely to be more effective at eliciting appropriate immune responses.

In order to manufacture a pharmaceutical product of this nature, the fluorocarbon-linked peptides must be synthesised, purified, blended together at appropriate ratios, rendered sterile and presented in a homogenous format suitable for administration.

SUMMARY OF THE INVENTION

The present inventors have found that fluorocarbon-linked peptides are often poorly soluble in aqueous media, such as water or phosphate buffered saline, even when the unlinked peptides are soluble in aqueous media. They have further found that the length and hydrophobicity of the peptide component of the fluorocarbon-linked peptide affects the solubility of the fluorocarbon-linked peptide. In particular, fluorocarbon vectors linked to longer, more hydrophobic peptides that display better immunogenetic properties have been found to be particularly insoluble.

Fluorocarbon-linked peptides are amphiphilic and characteristically form multimolecular micellar-type structures in both polar (protic and aprotic) and non-polar solvents. Such structures are not typically formed by native unlinked peptides. However, the inventors have found that many fluorocarbon-linked peptides, especially those with the best immunogenic properties, have a tendency to form large visible aggregates in aqueous media and other solvents. The formation of such aggregates is unacceptable in a pharmaceutical manufacturing process, which requires the production of a homogeneous, characterisable formulation.

Having identified this problem, the present inventors have addressed it and devised a method for preparing fluorocarbon-linked peptide formulations in which supra-molecular structures that support the solubility of the fluorocarbon-linked peptides are maintained. The formulation process developed by the inventors makes it possible to manufacture a stable product comprising the immunogenic fluorocarbon-linked peptides that they have found to be problematic to formulate, which product is easy to reconstitute with an aqueous medium to obtain a pharmaceutically acceptable solution.

In particular, the inventors have found that using an acidic solution promotes micelle formation and avoids the formation of insoluble aggregates. The solubilised fluorocarbon-linked peptides can be sterilised by filtration without loss of the fluorocarbon-linked peptides from the solution. After freeze drying, typically in the presence of a cryoprotectant, the fluorocarbon-linked peptides can be stored in a stable form and dissolved in an aqueous medium to obtain a pharmaceutically acceptable solution for administration.

The inventors have found that acetic acid is a particularly appropriate solvent for a wide range of fluorocarbon-linked peptides, despite the high degree of variability in charge and hydrophobicity of the different peptides. Acetic acid is therefore also particularly suitable for solubilising a mixture of fluorocarbon-linked peptides.

Accordingly, the invention provides an aqueous acidic formulation suitable for use as in the preparation of a pharmaceutically acceptable fluorocarbon-linked peptide formulation, which formulation comprises a first fluorocarbon-linked peptide, wherein:
  (i) the peptide linked to the fluorocarbon is at least 20 amino acid residues long, comprises at least 50% hydrophobic amino acid residues and has an isoelectric point greater than or equal to 7; and
  (ii) the fluorocarbon-linked peptide is present in micelles with a diameter of less than 0.22 µm.

Preferably, the formulation comprises acetic acid. The aqueous formulation may have, for example, a pH of 5 or less.

The formulation may comprise one or more further fluorocarbon-linked peptide present in micelles with a diameter of less than 0.22 µm. Preferably at least 80% of the fluorocarbon-linked peptide micelles present in the formulation have a diameter of less than 100 nm.

In one embodiment, the formulation according to the invention does not comprise a fluorocarbon-linked peptide in which the peptide linked to the fluorocarbon: (i) has an isoelectric point of less than 7; (ii) does not comprise a positively charged amino acid in the last 15 contiguous amino acids distal to the fluorocarbon; and/or (iii) comprises a contiguous sequence of 20 amino acid residues comprising more than 80% hydrophobic amino acid residues.

The peptides linked to the fluorocarbons are typically immunogenic peptides derived from a pathogen, autologous protein or tumor cell. The formulation according to the invention may further comprise a pharmaceutically acceptable carrier or diluent and/or an adjuvant.

The invention also provides:

A method for obtaining a pharmaceutically acceptable fluorocarbon-linked peptide formulation, said method comprising:
  (i) solubilising a fluorocarbon-linked peptide in acetic acid;
  (ii) filter-sterilising the solubilised fluorocarbon-linked peptide; and
  (iii) drying the filter-sterilised fluorocarbon-linked peptide.

a fluorocarbon-linked peptide formulation obtainable by a method according to the invention;

a pharmaceutically acceptable formulation comprising six fluorocarbon-linked peptides, wherein the peptides linked to the fluorocarbons comprise the sequences set out in SEQ ID NOs: 1 to 6 and wherein the formulation comprises no other fluorocarbon-linked peptides;

a pharmaceutically acceptable formulation according to the invention use in a method of treatment of the human or animal body by therapy;

a pharmaceutically acceptable formulation according to the invention for use in a method of treating or preventing a pathogenic infection, an autoimmune disease or cancer;

use of a pharmaceutically acceptable formulation according the invention in the manufacture of a medicament for treating or preventing a pathogenic infection, an autoimmune disease or cancer; and a method of treating or preventing a pathogenic infection, an autoimmune disease or cancer, said method comprising administering to an individual in need thereof an effective amount of a pharmaceutically acceptable formulation according to the invention.

BRIEF DESCRIPTION OF THE FIGURES

FIG. 3 is a table showing the results of a visual examination of individual FCPs solubilised in various solvents. Following vortexing each solution was visually examined for clarity, with a score of "+++" assigned for a clear solution through to a score of "−" for a highly cloudy solution. The degree of foam formation and the presence of particulates were also recorded, with "+++" indicating high levels and "−" indicating absence of each. "*" indicates that the solution became viscous.

FIG. 4 is a table showing the results of a visual examination of individual FCPs solubilised in various solvents after dilution with a mannitol solution. Each solution was visually examined for clarity, with a score of "+++" assigned for a clear solution through to a score of "−" for a highly cloudy solution. The degree of foam formation and the presence of particulates were also recorded with "+++" indicating high levels and "−" indicating absence of each.

FIG. 7 shows the size distributions by volume of fluorocarbon-linked peptide particles before (A) and after (B) sterilising grade filtration assessed by DLS.

BRIEF DESCRIPTION OF THE SEQUENCE LISTING

Figure 1:
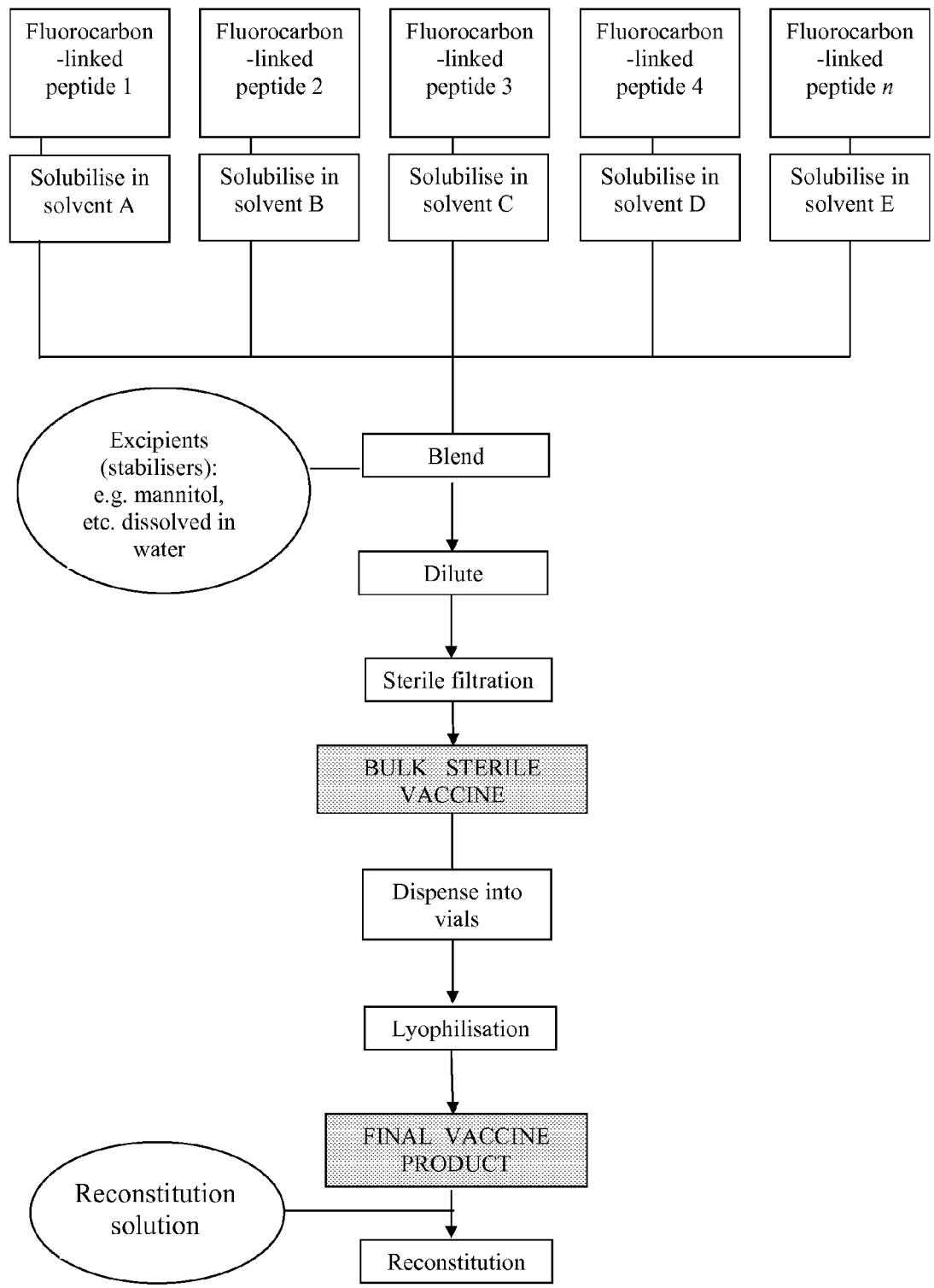
FIG. 1 shows an example of a typical fluorocarbon-linked peptide manufacturing process flow.
Figure 2:
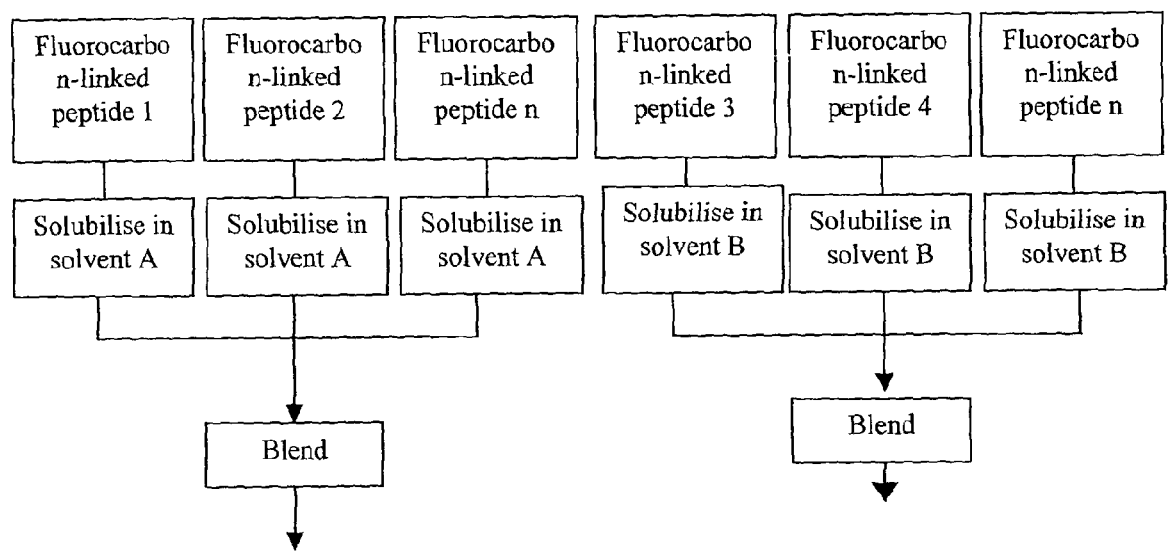
FIG. 2 shows an alternative fluorocarbon-linked peptide manufacturing process flow.

The sequence listing corresponds to the peptides used in the Examples as shown in the Table below.

| Sequence | Peptide |
| --- | --- |
| SEQ ID NO: 1 | P1 without N-terminal lysine |
| SEQ ID NO: 2 | P8 without N-terminal lysine |
| SEQ ID NO: 3 | P9 without N-terminal lysine |
| SEQ ID NO: 4 | P2 without N-terminal lysine |
| SEQ ID NO: 5 | P4 without N-terminal lysine |
| SEQ ID NO: 6 | P5 without N-terminal lysine |
| SEQ ID NO: 7 | P1 variant without N-terminal lysine |
| SEQ ID NO: 8 | P8 variant without N-terminal lysine |
| SEQ ID NO: 9 | P8 variant without N-terminal lysine |
| SEQ ID NO: 10 | P10 without N-terminal lysine |
| SEQ ID NO: 11 | P3 without N-terminal lysine |
| SEQ ID NO: 12 | P4 variant without N-terminal lysine |
| SEQ ID NO: 13 | P6 without N-terminal lysine |
| SEQ ID NO: 14 | P7 without N-terminal lysine |
| SEQ ID NO: 15 | P11 without N-terminal lysine |
| SEQ ID NO: 16 | P12 without N-terminal lysine |
| SEQ ID NO: 17 | P1 with N-terminal lysine |
| SEQ ID NO: 18 | P8 with N-terminal lysine |
| SEQ ID NO: 19 | P9 with N-terminal lysine |
| SEQ ID NO: 20 | P2 with N-terminal lysine |
| SEQ ID NO: 21 | P4 with N-terminal lysine |
| SEQ ID NO: 22 | P5 with N-terminal lysine |
| SEQ ID NO: 23 | P3 with N-terminal lysine |
| SEQ ID NO: 24 | P6 with N-terminal lysine |
| SEQ ID NO: 25 | P7 with N-terminal lysine |
| SEQ ID NO: 26 | P10 with N-terminal lysine |
| SEQ ID NO: 27 | P11 with N-terminal lysine |
| SEQ ID NO: 28 | P12 with N-terminal lysine |

DETAILED DESCRIPTION OF THE INVENTION

The present invention provides a method of formulating fluorocarbon-linked peptides for administration to a human or animal and pharmaceutically acceptable fluorocarbon-linked peptide formulations obtainable by the method of the invention. The method of the invention comprises the step of solubilising the fluorocarbon-linked peptide in an acidic solution, preferably in acetic acid. The invention also provides aqueous formulations which are acidic and so unsuitable for administration to a human or animal but which are important for obtaining the pharmaceutically acceptable formulation.

Typically, at least one fluorocarbon-linked peptide used in the formulation process or present in the aqueous acidic formulation or pharmaceutically acceptable formulation of the invention comprises a peptide of at least 20 amino acid residues, having at least 50% hydrophobic amino acid residues and having an isoelectric point of greater than or equal to 7.

A formulation of the invention may comprise, or the formulation method of the invention may use, at least one fluorocarbon-linked peptide wherein the peptide comprises at least about 20 amino acids in which at least about 50% of the amino acids are hydrophobic. Other fluorocarbon-linked peptides present in the formulation may be shorter than 20 amino acids and/or may have fewer than 50% hydrophobic residues.

Formulations of the present invention may contain fluorocarbon-linked peptides comprising a sequence of at least seven amino acids up to about 100 amino acids, such as from about 9 to about 50 amino acids, preferably from about 15 to about 45 amino acids, more preferably from about 20 to about 40 amino acids, such as from about 25 to about 38, for example 30, 31, 32, 33, 34, 35, 36 or 37 amino acids.

The formulation of the invention may comprise at least one fluorocarbon-linked peptide, wherein at least 50% of the amino acids in the peptide are hydrophobic. Typically, between about 50% and about 80%, such as about 70% or about 75%, of residues are hydrophobic. The lower limit could be 48% or 49%. Preferably, the peptide comprises from about 55% to about 60 or about 65% hydrophobic residues.

Where the formulation comprises further fluorocarbon-linked peptides, the further fluorocarbon-linked peptides may have less than 50% hydrophobicity. For example, the peptide component of a further fluorocarbon-linked peptide may comprise from about 30% to about 70% hydrophobic residues, for example, about 40%, such as at about 45%, 50%, 55%, 60% or 65% hydrophobic residues. Tryptophan (W), tyrosine (Y), isoleucine (I), phenylalamine (F), leucine (L), valine (V), methionine (M), arginine (A), proline (P), glycine (G) and cysteine (C) are hydrophobic amino acids. In a preferred embodiment, none of the peptides present in the formulation comprise a contiguous sequence of 20 or more amino acid residues in which more than 80% of the residues are hydrophobic.

One or more of the further fluorocarbon-linked peptides may comprise a peptide that: is at least 20 amino acid residues long; comprises at least 50% hydrophobic amino acid residues; and/or has an isoelectric point greater than or equal to 7. The first fluorocarbon-linked peptide and/or one or more of the further fluorocarbon-linked peptides may comprise a peptide that: comprises a positively charged amino acid in the last 15 contiguous amino acids distal to the fluorocarbon; and/or does not comprise a contiguous sequence of 20 amino acid residues comprising more than 80% hydrophobic amino acid residues.

In one embodiment, none of the peptides in a formulation of the invention has an isoelectric point of less than 7, does not comprise a positively charged amino acid in the last 15 contiguous amino acids distal to the fluorocarbon, and/or comprises a contiguous sequence of 20 amino acid residues comprising more than 80% hydrophobic amino acid residues.

The fluorocarbon-linked peptides in the formulation of the invention are typically present in micelles with a diameter of less than 0.22 μm. The micelles typically have a diameter of from about 15 to about 200 nm, typically from about 20 nm to about 100 nm, such as from about 20 nm to about 30 nm or from about 30 nm to about 50 nm. However, some larger micelles may be present. In general, not more than 20%, such as from about 10% to about 15% of the aggregates have a diameter greater than 100 nm. Preferably, at least 80% of the fluorocarbon-linked peptide micelles have a diameter of less than 100 nm. Micelle size may be determined by any suitable method, such as by Dynamic Light Scattering (DLS) or using Transmission Electron Microscopy (TEM).

Formation of micelles may be facilitated by solubilising the fluorocarbon-linked peptides in an acidic solution. For example, the fluorocarbon-linked peptides may be solubilised in acetic acid as described herein. The aqueous formulation of the invention for use in the preparation of a pharmaceutically acceptable formulation may be acidic, having, for example, a pH of 5 or less.

The pharmaceutically acceptable formulation of the invention may be in dried, such as lyophilized, form. The pharmaceutically acceptable formulation of the invention may be an aqueous solution, for example an formed by dissolving a lyophilisate or other dried formulation in an aqueous medium. The aqueous solution is typically pH neutral.

In an aqueous (liquid) formulation of the invention, the solution is typically clear with no visible aggregates. In particular, no particulates are visible in the solution after perturbation by vortexing and sonication. This applies both to the acidic formulation and to the pharmaceutically acceptable formulation.

The peptide is typically a peptide antigen or allergen capable of inducing an immune response in an animal, including humans, i.e. the peptide is typically an immunogenic peptide. Preferably the immune response will have a beneficial effect in the host. Immunogenic peptides may be derived from an infectious agent (pathogen), such as a virus, bacterium, *mycobacterium*, parasite or fungus or from an autologous protein, such as a cancer antigen (protein derived from a tumour cell), or from an allergen.

Examples of viruses include and are not limited to animal and human viruses such as: influenza, Human Immunodeficiency Virus (HIV), Hepatitis C Virus (HCV), Hepatitis B Virus (HBV), Hepatitis A Virus (HAV), Respiratory Syncytial Virus (RSV), Venezuelan Equine Encephalitis virus (VEE), Japanese Encephalitis virus (JEV), Cytomegalovirus (CMV), Epstein Barr Virus (EBV), Herpes Virus (HSV-1 or HSV-2), Ebola, Marburg, Dengue, West Nile and Yellow fever viruses, Porcine reproductive and respiratory syndrome virus (PRRSV) and Feline Immunodeficiency Virus (Fly).

Examples of bacteria and mycobacteria include, but are not limited to *Mycobacterium tuberculosis, Legionella, Rickettsiae, Chlamydiae*, and *Listeria monocytogenes*.

Examples of parasites include, but are not limited to *Plasmodium falciparum* and other species of the Plasmodial family.

Examples of fungi include, but are not limited to *Candida albicans, Cryptococcus, Rhodotorula* and *Pneumocystis*.

Autologous or self-antigens include, but are not limited to the following antigens associated with cancers, P53, MAGE-A3, NY-ESO-1, SURVIVIN, WT1, HER-2/neu, MUC 1, hTERT, MAGE-1, LAGE-1, PAP, T21, TRP-2, PSA, Livin, HAGE, SSX-1, PRAME, PASD1, IMP-3, SSX-4, CDCA-1 and/or BAGE.

Allergens include, but are not limited to, phospholipase $A_2$ (API ml) associated with severe reactions to bee, Derp-2, Der p 2, Der f, Der p 5 and Der p 7 associated with reaction against the house-dust mite *Dermatophagoides pteronyssinus*, the cockroach allergen Bla g 2 and the major birch pollen allergen Bet v 1.

In one embodiment, the peptide is derived from the influenza virus. The influenza peptide antigen may comprise one or more epitopes from an influenza type A protein, an influenza type B protein or an influenza type C protein. Examples of the influenza virus proteins, from both the influenza A and B types, include: haemagglutinin, neuraminidase, matrix (M1) protein, M2, nucleoprotein (NP), PA, PB1, PB2, NS1 or NS2 in any such combination.

As used herein the term "immunogenic" refers to a molecule having the ability to be recognised by immunological receptors such as T cell receptor (TCR) or B cell receptor (BCR or antibody). The immunogenic peptide may be natural or non-natural, provided it presents at least one epitope, for example a T cell and/or a B cell epitope. The peptide may contain one or more T cell epitopes, including T helper cell epitopes and/or cytotoxic T lymphocyte (CTL) epitopes, and/or one or more B cell epitopes or combinations of T and B cell epitopes, such as MHC class I or MHC class II epitopes. Methods for identifying epitopes are well known in the art.

The peptide may comprise one or more epitopes. The peptide may comprise more than one epitope linked together. One such example is the use of fusion peptides where a promiscuous T helper epitope can be covalently linked to one or multiple CTL epitopes or one or multiple B cell epitope. As an example, the promiscuous T helper epitope could be the PADRE peptide, tetanus toxoid peptide (830-843) or influenza haemagglutinin, HA (307-319).

The epitopes may be overlapping linear epitopes so that the peptide comprises a cluster of densely packed multi-specific epitopes.

The terminus of the peptide that is not conjugated to the fluorocarbon attachment may be altered to promote solubility of the construct via the formation of micelles. For example, a positively charged amino acid could be added to the peptide in order to promote the assembly of micelles. Either the N-terminus or the C-terminus of the peptide may be coupled to the vector to create the construct. To facilitate large-scale synthesis of the construct, the N- or C-terminal amino acid residues of the peptide can be modified. When the desired peptide is particularly sensitive to cleavage by peptidases, the normal peptide bond can be replaced by a non-cleavable peptide mimetic. Such bonds and methods of synthesis are well known in the art.

Non-standard, non-natural amino acids can also be incorporated in peptide sequences provided that they do not interfere with the ability of the peptide to interact with MHC molecules and remain cross-reactive with T cells recognising the natural sequences. Non-natural amino acids can be used to improve peptide resistance to protease or chemical stability. Examples of non-natural amino acids include the D-amino acids and cysteine modifications.

The peptide may be derived by purification from the native protein or produced by recombinant technology or by chemical synthesis. Methods for the preparation of peptides are well known in the art.

It will be understood by vaccine designers that more than one peptide may be required to provide a broader prophylactic or immunotherapeutic effect. Such multi-component products are desirable since they are likely to be more effective at eliciting appropriate immune responses. For example, the optimal formulation of an influenza vaccine may comprise a number of peptide epitopes from different influenza proteins or the optimal formulation of an HIV immunotherapeutic may comprise a number of epitopes from different HIV proteins. Alternatively, multiple epitopes may be incorporated into a formulation in order to confer immunity against a range of pathogens. For example a respiratory infection vaccine may contain epitopes from influenza virus and respiratory syncytial virus.

A formulation of the invention may comprise multiple immunogenic peptides. Typically each peptide comprises a different epitope. Each peptide may be linked to a common fluorocarbon vector. More practically, combinations of fluorocarbon-linked peptides may be present in a formulation of the invention, wherein different peptides are independently linked to fluorocarbon chains. In a mixture of fluorocarbon-linked peptides, each peptide may be linked to a fluorocarbon chain of a single structure. Alternatively, the mixture may comprise peptides linked to fluorocarbon chains with different structures.

A formulation of the invention may comprise one or more fluorocarbon-linked peptides, preferably from about 2 to about 20, preferably about 3 to about 10. In particular embodiments the multi component vaccine may contain 4, 5, 6, 7, 8 or 9 fluorocarbon-linked peptides. This aids the generation of a multi-epitopic immune response.

The different peptides present in a multi-component product may be different antigens from the same pathogen, or may be antigens from different pathogens. Alternatively, the peptides may be different tumor antigens or antigens from different parts of an autologous protein.

Fluorocarbon-linked peptides comprising immunogenic influenza peptides are used in the Examples. The present invention is not limited to these particular peptides but extends to any immunogenic peptides having the properties described above. However, preferred formulations of the invention include one or more of the following six immunogenic influenza peptides that are selected from highly conserved segments of the PA, PB1, PB2, NP & M1 proteins:

(SEQ ID NO: 1)
HMAIIKKYTSGRQEKNPSLRMKWMMAMKYPITADK (SEQ ID NO: 2)
VAYMLERELVRKTRFLPVAGGTSSVYIEVLHLTQG (SEQ ID NO: 3)
YITRNQPEWFRNVLSIAPIMFSNKMARLGKGYMFE (SEQ ID NO: 4)
APIMFSNKMARLGKGYMFESKRMKLRTQIPAEMLA (SEQ ID NO: 5)
DQVRESRNPGNAEIEDLIFLARSALILRGSVAHKS (SEQ ID NO: 6)
DLEALMEWLKTRPILSPLTKGILGFVFTLTVPSER

The peptides are preferably each separately linked to a fluorocarbon vector. Particularly preferred formulations of the invention comprise all six of the above fluorocarbon-linked peptides and do not include fluorocarbon-linked peptides comprising peptides having the sequences shown in any one of SEQ ID NOs: 13, 14, 23 and 24. Other fluorocarbon-linked peptides may be included in the preferred formulations of the invention. However, it is preferred that the formulation comprises the six fluorocarbon-linked peptides described above and no other fluorocarbon-linked peptides.

One or more of the six peptides may be substituted by a variant peptide comprising one, two or three amino acid substitutions. The variant peptides may comprises a sequence derived from different influenza strains. For example, SEQ ID NO: 1 may be replaced by SEQ ID NO: 7, SEQ ID NO: 2 may be replaced by SEQ ID NO: 8 or 9, SEQ ID NO: 3 may be replaced by SEQ ID NO: 10, SEQ ID NO: 4 by SEQ ID NO: 11 and/or SEQ ID NO: 5 by SEQ ID NO: 12.

The peptides may be linked to the fluorocarbon vector via a spacer moiety as described below. The spacer moiety is preferably a lysine residue. Accordingly, the preferred formulation of the invention may comprise fluorocarbon-linked peptides in which the peptides have one or more of the sequences shown in SEQ ID NOs: 17 to 22. The N-terminal lysine in the peptides is preferably linked to a fluorocarbon having the formula $C_8F_{17}(CH_2)_2COOH$. The fluorocarbon is preferably coupled to the epsilon chain of the N-terminal lysine residue.

Thus, in one preferred embodiment, the invention provides a pharmaceutically acceptable formulation consisting of, or consisting essentially of, six fluorocarbon-linked peptides comprising SEQ ID NOs: 1 to 6 and a pharmaceutically acceptable carrier or diluent and optionally an adjuvant.

In each of the six fluorocarbon-linked peptides, the peptides preferably consist of one of SEQ ID NOs: 1 to 6 with an N-terminal lysine residue added (i.e. one of SEQ ID NOs: 17 to 22), which lysine residue is coupled to a fluorocarbon chain having the formula $C_8F_{17}(CH_2)_2COOH$ via the epsilon chain of the lysine residue.

The fluorocarbon attachment in the fluorocarbon-linked peptide may comprise one or more chains derived from perfluorocarbon or mixed fluorocarbon/hydrocarbon radicals, and may be saturated or unsaturated, each chain having from 3 to 30 carbon atoms.

Thus, the chains in the fluorocarbon attachment are typically saturated or unsaturated, preferably saturated. The chains in the fluorocarbon attachment may be linear or branched, but are preferably linear. Each chain typically has from 3 to 30 carbon atoms, preferably from 5 to 25, more preferably from 8 to 20.

In order to covalently link the fluorocarbon attachment to the peptide, a reactive group, or ligand, for example —CO—, —NH—, S, O or any other suitable group is included. The use of such ligands for achieving covalent linkages is well known in the art. The reactive group may be located at any position on the fluorocarbon molecule.

Coupling of the fluorocarbon moiety to the peptide may be achieved through functional groups such as —OH, —SH, —COOH and $—NH_2$ naturally present or introduced onto any site of the peptide. Examples of such linkages include amide, hydrazone, disulphide, thioether and oxime bonds.

Optionally, a spacer element (peptidic or non-peptidic) may be incorporated to permit cleavage of the peptide from the fluorocarbon element for processing within an antigen-presenting cell and to optimise steric presentation of the peptide. The spacer may also be incorporated to assist in the synthesis of the molecule and to improve its stability and/or solubility. Examples of spacers include polyethylene glycol (PEG) or amino acids such as lysine or arginine that may be cleaved by proteolytic enzymes.

In one embodiment, the fluorocarbon-linked peptide may have the chemical structure $C_mF_n—C_yH_x—(Sp)-R$ or derivatives thereof, where m=3 to 30, $n \leq 2$ m+1, y=0 to 15, $x \leq 2y$, (m+y)=3 to 30 and Sp is an optional chemical spacer moiety and R is a peptide antigen. Typically m and n satisfy the relationship $2m-1 \leq n \leq 2$ m+1, and preferably n=2 m+1. Typically x and y satisfy the relationship $2y-2 \leq x \leq 2y$, and preferably x=2y. Preferably the $C_mF_n—C_yH_x$ moiety is linear.

It is preferred that m is from 5 to 15, more preferably from 8 to 12. It is also preferred that y is from 0 to 8, more preferably from 0 to 6 or 0 to 4. It is therefore particularly preferred that the moiety is saturated (i.e. n=2m+1 and x=2y) and linear, and that m=8 to 12 and y=0 to 6 or 0 to 4.

In a particular example, the fluorocarbon attachment is derived from 2H, 2H, 3H, 3H-perfluoroundecanoic acid of the following formula:

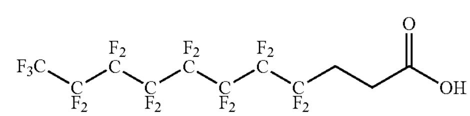 [SMILES: O=C(O)CCC(F)(F)C(F)(F)C(F)(F)C(F)(F)C(F)(F)C(F)(F)C(F)(F)C(F)(F)F]

Thus, a preferred fluorocarbon attachment is the linear saturated moiety $C_8F_{17}(CH_2)_2—$.

Further examples of fluorocarbon attachments have the following formulae: $C_6F_{13}(CH_2)_2—$, $C_7F_{15}(CH_2)_2—$, $C_9F_{19}(CH_2)_2—$, $C_{10}F_{21}(CH_2)_2—$, $C_5F_{11}(CH_2)_3—$, $C_6F_{13}(CH_2)_3—$, $C_7F_{15}(CH_2)_3—$, $C_8F_{17}(CH_2)_3—$ and $C_9F_{19}(CH_2)_3—$ which are derived from $C_6F_{13}(CH_2)_2COOH$, $C_7F_{15}(CH_2)_2COOH$, $C_9F_{19}(CH_2)_2COOH$, $C_{10}F_{21}(CH_2)_2COOH$, $C_5F_{11}(CH_2)_3COOH$, $C_6F_{13}(CH_2)_3COOH$, $C_7F_{15}(CH_2)_3COOH$, $C_8F_{17}(CH_2)_3COOH$ and $C_9F_{19}(CH_2)_3COOH$ respectively.

Preferred examples of suitable structures for the fluorocarbon vector-antigen constructs have the formula:

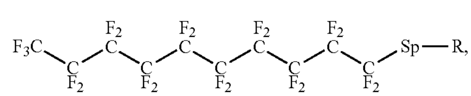

or

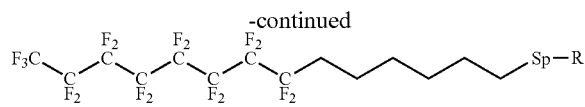

in which Sp and R are as defined above. Preferably Sp is derived from a lysine residue and has the formula —CONH—(CH$_2$)$_4$—CH(NH$_2$)—CO—. Preferably R is any one of SEQ ID NOs: 1 to 6. The amino group of the N-terminal amino acid of SEQ ID NO: 1, 2, 3, 4, 5 or 6 thus forms an amide linkage with the C-terminal carboxy group of the spacer of formula —CONH—(CH$_2$)$_4$—CH(NH$_2$)—CO—.

In the context of the current invention the fluorocarbon attachment may be modified such that the resulting compound is still capable of delivering the peptide to antigen presenting cells. Thus, for example, a number of the fluorine atoms may be replaced with other halogen atoms such as chlorine, bromine or iodine. In addition, it is possible to replace a number of the fluorine atoms with methyl groups and still retain the properties of the molecule described herein.

The present invention provides both an acidic aqueous formulation and a pharmaceutically acceptable formulation comprising one or more, such as two or more, fluorocarbon-linked peptides and optionally a pharmaceutically acceptable carrier or excipient. Preferably, at least one fluorocarbon-linked peptide in the formulation comprises a peptide of at least 20 amino acid residues, having at least 50% hydrophobic amino acid residues and having an isoelectric point of greater than or equal to 7. The excipient may be a stabilizer or bulking agent necessary for efficient lyophilisation. Examples include sorbitol, mannitol, polyvinylpyrrolidone and mixtures thereof, preferably mannitol. Other excipients that may be present include preservatives such as antioxidants, lubricants, cryopreservatives and binders well known in the art.

The present invention provides a method for preparing the formulations of the invention.

In a method of the invention, at least one fluorocarbon-linked peptide is solubilised in acetic acid as a first step in formulating a pharmaceutical product. The fluorocarbon-linked peptide used as a starting material is typically in desiccated form. The fluorocarbon-linked peptide(s) solubilised in acetic acid typically comprises a peptide that is at least about 20 amino acids long in which at least about 50% of the amino acids are hydrophobic. Other fluorocarbon-linked peptides may be solubilised in acetic acid or in other solvents. In particular, fluorocarbon-linked peptides that comprise peptides shorter than 20 amino acids and/or that have fewer than 50% hydrophobic residues may be solubilised in a solvent other than acetic acid.

The term "solubilisation" is used herein to mean the dispersion of fluorocarbon-linked peptides in a solvent to form a visually clear solution that does not lose material upon sterile filtration. The fluorocarbon-linked peptides may be present in a multimolecular micellar structure. By "dispersion" is meant dissolution of the lyophilized fluorocarbon-linked peptides in order to disrupt particulates and achieve solubility through the formation of micellar structures.

The term "aggregates" is used herein to describe macromolecular fluorocarbon-linked peptide structures. Micellar aggregates of fluorocarbon-linked peptides may assist in solubilisation. Gross aggregates of fluorocarbon-linked peptides result in visible particulates. The term "particulates" is used herein to mean aggregates of fluorocarbon-linked peptides visible to the naked eye.

Solubilisation of the fluorocarbon-linked peptide in acetic acid typically results in the formation of a clear solution containing micellar aggregates of fluorocarbon-linked peptides. The micellar aggregates typically have a diameter of from about 20 nm to about 50 nm, for example from about 17 nm to about 30 nm. However, some larger aggregates having a diameter of more than about 50 nm, typically not more than 20%, such as from about 10 to about 15% of the aggregates have a diameter greater than 100 nm. Preferably, no aggregates are visible to the naked eye. Particle size may be determined by any suitable method, such as by Dynamic Light Scattering (DLS) or using Transmission Electron Microscopy (TEM). For example, using TEM in negative staining, 20 μl of fluorocarbon-linked peptide solution is deposited on a Formvar carbon coated copper electron microscope grid (300 mesh). 200 of uranyle acetate (1% aqueous) is then added. After 30 seconds, excess solution is quickly wicked away with a Whatman filter paper. The sample is then allowed to dry for at least 2 minutes before analysis. Transmission electron microscopy is then performed on Philips CM120 biotwin at 120 kV accelerating voltage. Image acquisition is performed at a direct magnification ranging from 50000× to 150000×.

The concentration of fluorocarbon-linked peptide in the solution is typically from about 0.1 mM to about 10 mM, such as about 0.5 mM, 1 mM, 2 mM, 2.5 mM or 5 mM. An example of a suitable concentration is about 10 mg/ml.

Examples of typical manufacturing process flows, commencing at the initial solubilisation step through to final product presentation are provided in FIGS. 1 and 2. These emphasise the requirement for the solvent to not only achieve fluorocarbon-linked peptide solubility but also for it to be compatible with downstream processes including blending with potential stabilizers, sterile filtration and lyophilisation. In the flowcharts the letter n is used to denote a variable number of additional fluorocarbon-linked peptides that could be included in the formulation.

Variations to the process flow are permitted, as known to one skilled in the art, to achieve the same resulting product characteristics; namely, that the input components are blended homogenously together to the desired ratios with any aggregates dispersed, rendered sterile and presented in a suitable format for administration. Such examples could include the introduction of a vortexing and/or sonication post-blending or post-dilution stage to facilitate solubilisation. Other permutations of the manufacturing process flow could include sterile filtration being performed at an earlier stage of the process or the omission of lyophilisation to permit a liquid final presentation.

Alternatively, one set of fluorocarbon-linked peptides may be solubilised individually in one organic solvent, then blended together and sterile filtered, with a second set of fluorocarbon-linked peptides being solubilised in an alternative solvent, blended and sterile filtered (FIG. 2) before the two sets of fluorocarbon-linked peptides are blended together for further processing.

The initial solvent may be the same or different for each fluorocarbon-linked peptide so that one of more of the fluorocarbon-linked peptides may be solubilised in acetic acid and one or more of the fluorocarbon-linked peptides may be solubilised in another solvent having acceptable properties. For example in the Process Flow of FIG. 1, B may be a different solvent to A.

Alternatively, acetic acid may be used as the initial solvent for different fluorocarbon-linked peptides, but may be used at different, optimised, concentrations for the different fluorocarbon-linked peptides. For example in the Process Flow of FIG. 1, B may be a different concentration of the same solvent as A.

The different fluorocarbon-linked peptides may be mixed prior to solulilisation.

The acetic acid may be used at a concentration of from 5 to 80% (v/v) aqueous acetic acid, such as at a concentration of from 10 to 70% (v/v), such as a concentration of about 20% (v/v) or 50% (v/v). In a method for formulating a mixture of fluorocarbon-linked peptides, different peptides may be solubilised in different concentrations of acetic acid prior to blending. For example, one or more fluorocarbon-linked peptide may be solubilised in 10% (v/v) acetic acid and one or more peptide may be solublised in 80% (v/v) acetic acid.

Where more than one solvent is used in the manufacturing process, each solvent used is typically: able to solubilise the fluorocarbon-linked peptide it is being used to solubilise at relatively high concentrations (for example, up to 10 millimolar, such as up to 2 millimolar); water-miscible to facilitate dilution with water prior to lyophilisation; compatible with lyophilisation stabilizers, such as mannitol, that may be used in the manufacturing process; has a safety profile acceptable to the pharmaceutical regulatory authorities, for example, complies with the requirements of ICH Q3C (Note for Guidance on Impurities: Residual Solvents) and the requirements of Class III solvents, as defined by USP Residual Solvents <467> (residual solvent limit of 50 mg/day in finished product or less than 5000 ppm or 0.5%); amenable to lyophilisation, that is, sufficiently volatile to be removed to safe levels upon lyophilisation; able to disperse the fluorocarbon-linked peptide molecules efficiently in a reproducible and uniform manner such that yield losses on sterilising grade filtration are minimised; unable to react with, or promote degradation of, the fluorocarbon-linked peptide molecule; and/or compatible with the materials routinely used in pharmaceutical product manufacture (containers/filter membranes/pipework etc).

Examples of solvents that may be used to disperse one or more of the fluorocarbon-linked peptides in the blend include phosphate buffered saline (PBS), propan-2-ol, tert-butanol, acetone and other organic solvents.

Where the different fluorocarbon-linked peptides are solubilised separately, for example in different solvents or in different concentrations of acetic acid, the solubilised peptides are blended to create a mixture of fluorocarbon-linked peptides.

One or more pharmaceutically acceptable excipients and/or adjuvants may also be added to the solubilised fluorocarbon-linked peptide or mixture of fluorocarbon-linked peptides.

By "excipient" is meant an inactive substance used as a carrier for the fluorocarbon-linked peptides. Typically, the solubilised fluorocarbon-linked peptides are mixed with the excipient. Potential excipients that may be used in the manufacturing process include stabilizers or bulking agents necessary for efficient lyophilisation. Examples include sorbitol, mannitol, polyvinylpyrrolidone and mixtures thereof, preferably mannitol. Other excipients include preservatives such as antioxidants, lubricants, cryopreservatives and binders well known in the art.

To enhance the breadth and intensity of the immune response mounted to the peptide antigen, one or more adjuvant and/or other immuno-potentiating agent may be included in the formulation. An "adjuvant" in this context is an agent that is able to modulate the immune response directed to a co-administered antigen while having few if any direct effects when given on its own. Such adjuvants may be capable of potentiating the immune response in terms of magnitude and/or cytokine profile.

Suitable adjuvants include:

(1) natural or synthetically derived refinements of natural components of bacteria such as Freund's adjuvant & its derivatives, muramyldipeptide (MDP) derivatives, CpG, monophosphoryl lipid A;

(2) other known adjuvant or potentiating agents such as saponins, aluminium salts and cytokines;

(3) oil in water adjuvants, such as the submicron oil-in water emulsion MF-59, water-in-oil adjuvants, immuno-stimulating complex (ISCOMs), liposomes, formulated nano- and micro-particles;

(4) bacterial toxins and toxoids; and (5) other useful adjuvants well known to one skilled in the art.

After solubilisation and blending the solution of fluorocarbon-linked peptide(s) is diluted. For example, the blend may be diluted in water.

The solution containing the fluorocarbon-linked peptides is preferably sterilised. Sterilisation is particularly preferred where the formulation is intended for systemic use. Any suitable means of sterilisation may be used, such as UV sterilisation or filter sterilisation. Preferably, filter sterilisation is used. Sterile filtration may include a 0.45 µm filter followed by a 0.22 µm sterilizing grade filter train.

Sterilisation may be carried out before or after addition of any excipients and/or adjuvants.

After filter sterilisation, the yield of the fluorocarbon-linked peptide present in the sterile solution is typically at least 80%, preferably at least 90%, more preferably at least 95% of the amount of fluorocarbon-linked peptide present before sterilisation. A yield of more than 95%, such as a yield of 98%, 99% or more, such as a yield of 100%, may be achieved.

After sterilisation, the fluorocarbon-linked peptide is typically present in the solution in micellar structures having diameters of from about 20 nm to about 100 nm, such as about 30 nm or about 50 nm. Larger particles present in the solution prior to sterilisation may typically be reshaped by filter sterilisation. The sterilized solution may be stored in a sterile container.

The sterile formulation is dried to remove the acetic acid. Drying the formulation also facilitates long-term storage. Any suitable drying method may be used. Lyophilisation is preferred but other suitable drying methods may be used, such as vacuum drying, spray-drying, spray freeze-drying or fluid bed drying. The drying procedure can result in the formation of an amorphous cake within which the fluorocarbon-linked peptides are incorporated.

For long-term storage, the sterile formulation may be lyophilized. Lyophilisation can be achieved by freeze-drying. Freeze-drying typically includes freezing and then drying. For example, the fluorocarbon-linked peptide mixture may be frozen for 2 hours at −80° C. and freeze-dried in a freeze drying machine for 24 hours.

Pharmaceutically acceptable formulations of the invention may be solid compositions. The fluorocarbon-linked peptide composition may be obtained in a dry powder form. A cake resulting from lyophilisation can be milled into powder form. A solid composition according to the invention thus may take the form of free-flowing particles. The solid composition is typically provided as a powder in a sealed vial, ampoule or syringe. If for inhalation, the powder can be provided in a dry powder inhaler. The solid matrix can alternatively be provided as a patch. A powder may be compressed into tablet form.

The dried, for example lyophilized, fluorocarbon-linked peptide formulation may be reconstituted prior to administration. The term "reconstitution" as used herein means dissolution of the dried vaccine product prior to use. Following drying, such as lyophilisation, the fluorocarbon-linked peptide product is preferably reconstituted to form an isotonic, pH neutral, homogeneous suspension. The formulation is typically reconstituted in the aqueous phase, for example by adding Water for Injection (Hyclone), histidine buffer solution (such as 28 mM L-histidine buffer) or phosphate buffered saline (PBS). The reconstituted formulation is typically dispensed into sterile containers, such as vials, syringes or any other suitable format for storage or administration.

The invention provides a fluorocarbon-linked peptide formulation obtainable by a method according to the invention. The formulation may be an intermediate in the preparation of a pharmaceutical product.

The invention provides an aqueous formulation suitable for use as an intermediate in the preparation of a fluorocarbon-linked peptide formulation for administration to a human or animal, which aqueous composition is acidic and comprises one or more solubilised fluorocarbon-linked peptide as described above. The acidic solution typically comprises acetic acid. At least one of the fluorocarbon-linked peptides may be at least 20 amino acid residues long, comprise at least 50% hydrophobic amino acid residues and have an isoelectric point greater than or equal to 7; and/or be present in micelles with a diameter of less than 0.22 µm. The aqueous solution is preferably sterile. It may further comprise a pharmaceutically acceptable carrier or diluent.

The invention also provides a pharmaceutically acceptable fluorocarbon-linked peptide formulation. The pharmaceutically acceptable formulation may be a solid, such as a powder, cake or tablet. The pharmaceutical formulation may be an aqueous solution.

The formulation may be stored in a container, such as a sterile vial or syringe.

The invention thus provides, in one embodiment, a formulation comprising a fluorocarbon-linked peptide, wherein the fluorocarbon-linked peptide is present in micellar structures, and a pharmaceutically acceptable amount of acetic acid. In other formulations of the invention, the acetic acid is completely removed by the drying step.

The ICH recommended maximum of acetic acid is 50 mg per day. Typically, the acetate level in a formulation of the invention is less than 5000 ppm or 0.5% in accordance with the requirements for Class III solvents defined by USP Residual Solvents <467>. The invention also provides an intermediate formulation comprising a fluorocarbon-linked peptide solubilised in acetic acid.

In one aspect, the present invention provides a formulation comprising two or more fluorocarbon-linked peptides, wherein the fluorocarbon-linked peptides are present in micellar structures.

In another aspect, the invention provides a formulation comprising a fluorocarbon-linked peptide, wherein the fluorocarbon-linked peptide is present in micellar structures and the formulation is in lyophilised form.

In a formulation of the invention, the fluorocarbon-linked peptides are typically present in multiple micellar structures. The micellar structures typically have a diameter of from about 20 nm to about 100 nm, such as about 50 nm or 70 nm. It is preferred than at least 80%, such as at least 90% or at least 95% of the micellar structures present in the formulation have a diameter of less than 100 nm such as a diameter of from about 20 nm to about 50 nm.

In a further aspect, the formulation of the present invention further comprises a pharmaceutically acceptable excipient and/or adjuvant. For example, in one embodiment the formulation further comprises mannitol and/or other excipients.

In another aspect the invention provides the use of the formulation of the invention in the manufacture of a medicament for inducing an immune response in a human or animal. The invention also provides the use of the formulation of the invention in the manufacture of a medicament for treating or preventing of a disease of the human or animal body.

In a further aspect, the invention provides the formulation of the invention for use in a method of treating the human or animal body by therapy. Also provided in the formulation of the invention for use in a method of stimulating an immune response in a human or animal and the formulation of the invention for use in a method of for treating or preventing of a disease of the human or animal body.

In a further aspect, the invention provides a method of inducing an immune response in a human or animal in need thereof, said method comprising administering to said human or animal a prophylactic or therapeutic amount of a formulation of the present invention. The immune response may be effective in the treatment or prevention of a disease.

The disease is typically an infectious disease, an autoimmune disease, an allergy, a hormonal disease or cancer. The fluorocarbon-linked peptide in the formulation is selected to include one or more epitopes from the pathogen causing the infectious disease, the autologous protein implicated in the autoimmune disease or hormonal disease, the allergen responsible for the allergy or a tumor antigen expressed on the cancer cells.

Examples of infectious diseases that may be treated or prevented using a fluorocarbon-linked peptide formulation of the invention include, but are not restricted to, infections caused by the following viruses, bacteria, mycobacteria, parasites and fungi: influenza, Human Immunodeficiency Virus (HIV), Hepatitis C Virus (HCV), Hepatitis B Virus (HBV), Hepatitis A Virus (HAV), Respiratory Syncytial Virus (RSV), Venezuelan Equine Encephalitis virus (VEE), Japanese Encephalitis virus (JEV), Cytomegalovirus (CMV), Epstein Barr Virus (EBV), Herpes Virus (HSV-1 or HSV-2), Ebola, Marburg, Dengue, West Nile and Yellow fever viruses, Porcine reproductive and respiratory syndrome virus (PRRSV), Feline Immunodeficiency Virus (FIV), *Mycobacterium tuberculosis, Legionella, Rickettsiae, Chlamydiae,* and *Listeria monocytogenes, Plasmodium falciparum* and other species of the Plasmodial family, *Candida albicans, Cryptococcus, Clostridium tetani, Rhodotorula* and *Pneumocystis.*

Examples of cancers that may be treated or prevented using a fluorocarbon-linked peptide formulation of the invention include breast cancer, melanoma, colorectal cancer nasopharyngeal carcinoma, Burkitt's lymphoma and other human cancers.

In a preferred embodiment the formulation of the invention is used to treat or vaccinate against influenza. In a further aspect of this embodiment, the influenza vaccine formulation may be administered in combination with an anti-viral therapeutic composition, including neuraminidase inhibitor treatments such as amanidine, rimantidine, zanamivir or oseltamivir. In a still further aspect, the influenza vaccine formulation may be administered in combination with other influenza vaccines, such as conventional antibody generating influenza vaccines. The other influenza vaccine is preferably a seasonal influenza vaccine.

Administration may be contemporaneous or separated by time. The pharmaceutically acceptable formulation of the invention may be administered before, together with or after the anti-viral therapeutic composition and/or other influenza vaccine.

The formulations comprising influenza peptides, in particular the six influenza peptides having the sequences shown in SEQ ID NOs: 1 to 6, are provided for use in a method of vaccinating against influenza. Accordingly, pharmaceutically acceptable formulations of the invention comprising such peptide may be used in the manufacture of a medicament for treating or preventing influenza. The invention also provides a method of treating or preventing influenza, which method comprises administering to a subject in need thereof a therapeutically effective amount of the fluorocarbon-linked influenza peptide formulations of the invention.

Formulations of the invention may be administered to a human or animal subject in vivo using a variety of known routes and techniques. For example, the formulation may be provided as an injectable solution, suspension or emulsion and administered via parenteral, subcutaneous, oral, epidermal, intradermal, intramuscular, interarterial, intraperitoneal, intravenous injection using a conventional needle and syringe, or using a liquid jet injection system. The formulation may be administered topically to skin or mucosal tissue, such as nasally, intratrachealy, intestinally, sublingually, rectally or vaginally, or provided as a finely divided spray suitable for respiratory or pulmonary administration.

In one embodiment, the method of the invention further comprises the step of processing the mixture into a formulation suitable for administration as a liquid injection. Preferably, the method further comprises the step of processing the mixture into a formulation suitable for administration via ingestion or via the pulmonary route.

The formulation is administered to a subject in an amount that is compatible with the dosage formulation and that will be prophylactically and/or therapeutically effective. The administration of the formulation of the invention may be for either "prophylactic" or "therapeutic" purpose. As used herein, the term "therapeutic" or "treatment" includes any one or more of the following: the prevention of infection or reinfection; the reduction or elimination of symptoms; and the reduction or complete elimination of a pathogen. Treatment may be effected prophylactically (prior to infection) or therapeutically (following infection).

The choice of carrier if required is frequently a function of the route of delivery of the composition. Within this invention, compositions may be formulated for any suitable route and means of administration. Pharmaceutically acceptable carriers or diluents include those used in formulations suitable for oral, ocular, rectal, nasal, topical (including buccal and sublingual), vaginal or parenteral (including subcutaneous, intramuscular, intravenous, intradermal, transdermal) administration.

The formulation may be administered in any suitable form, for example as a liquid, solid, aerosol, or gas. For example, oral formulations may take the form of emulsions, syrups or solutions or tablets or capsules, which may be enterically coated to protect the active component from degradation in the stomach. Nasal formulations may be sprays or solutions. Transdermal formulations may be adapted for their particular delivery system and may comprise patches. Formulations for injection may be solutions or suspensions in distilled water or another pharmaceutically acceptable solvent or suspending agent.

The appropriate dosage of the vaccine or immunotherapeutic to be administered to a patient will be determined in the clinic. However, as a guide, a suitable human dose, which may be dependent upon the preferred route of administration, may be from 1 to 1000 µg, such as about 100 µg, 200 µg or 500 µg. Multiple doses may be required to achieve an immunological or clinical effect, which, if required, will be typically administered between 2 to 12 weeks apart. Where boosting of the immune response over longer periods is required, repeat doses 1 month to 5 years apart may be applied.

The following Examples illustrate the invention.

Example 1

Synthesis of Peptides

Peptides having the amino acid sequences shown in SEQ ID NOs: 1 to 6, 10, 11 and 13 to 16 were synthesised. The synthesis of each peptide was performed on solid phase using a classical Fmoc/t-butyl strategy and a TentaGel HL NH2 resin. A lysine residue was added to the N-terminus of each sequence. The sequences with the N-terminal lysine residue added are shown in SEQ ID NOS: 17 to 28. After the addition of an N-terminal Lysinyl residue, the resin block was split into two parts. One part was used to incorporate the fluorocarbon chain ($C_8F_{17}(CH_2)_2COOH$) on the epsilon-chain of the N-terminal lysine to derive the fluorocarbon-linked peptide (FCP). With the second part, acetylation of the epsilon-chain of the N-terminal lysine was performed to derive the native peptide for use in comparative studies. Purified fluorocarbon-linked peptide (FCP) and native peptides were obtained through cleavage in the presence of trifluoroacetic acid (TFA) and a final purification by reverse phase-high performance liquid chromatography (RP-HPLC). Both the FCPs and the native peptides described below possess an amido-group at the C-terminus. All preparations had a purity of 95% or greater and were presented a dry, lyophilised powder. Net peptide mass was calculated based on nitrogen content analysis.

The following peptides P1 to P12 were linked to a fluorocarbon chain to create the FCPs, or were acetylated to create the native peptides (the standard single letter code representation of amino acids has been used; X=Fluorocarbon vector (fluorocarbon-linked peptides); Z=acetyl (native peptides)):

P1:
NH2-K(X or Z)HMAIIKKYTSGRQEKNPSLRMKWMMAMKYPITAD K-CONH2

P2:
NH2-K(X or Z)APIMFSNKMARLGKGYMFESKRMKLRTQIPAEMLA-CONH2

P3:
NH2-K(X or Z)APIMFSNKMARLGKGYMFESKSMKLRTQIPAEMLA-CONH2

P4:
NH2-K(X or Z)DQVRESRNPGNAEIEDLIFLARSALILRGSVAHKS-CONH2

P5:
NH2-K(X or Z)DLEALMEWLKTRPILSPLTKGILGFVFTLTVPSER-CONH2

P6:
NH2-K(X or Z)SPGMMMGMFNMLSTVLGVSILNLGQKKYTKTTY-CONH2

-continued

P7:
NH2-K(X or Z)KKKSYINKTGTFEFTSFFYRYGFVANFSMELPSFG-

CONH$_2$

P8:
NH2-K(X or Z)VAYMLERELVRKTRFLPVAGGTSSVYIEVLHLTQG-

CONH$_2$

P9:
NH2-K(X or Z)YITRNQPEWFRNVLSIAPIMFSNKMARLGKGYMFE-

CONH$_2$

P10:
NH2-K(X or Z)YITKNQPEWFRNILSIAPIMFSNKMARLGKGYMFE-

CONH$_2$

P11:
NH2-K(X or Z)QSRMQFSSLTVNVRGSGMRILVRGNSPVFNYNK-

CONH$_2$

P12:
NH2-K(X or Z)PDLYDYKENRFIEIGVTRREVHIYYLEKANKIKSE-

CONH$_2$

The physiochemical properties of the native peptides are set out in Table 1 below. Residues considered to be hydrophobic are W, Y, I, F, L, V, M, A, P, G, and C. Charged residues are (+): K, R, H. (−): D, E

TABLE 1

Physicochemical Properties of Selected Peptides

| Peptide | Percentage Hydrophobic residues | Positive charges (including lysine residue added at N-terminus) | Negative charges |
|---|---|---|---|
| P1 | 51 | 10 | 2 |
| P2 | 60 | 8 | 2 |
| P3 | 60 | 7 | 2 |
| P4 | 49 | 7 | 5 |
| P5 | 60 | 5 | 4 |
| P6 | 61 | 4 | 0 |
| P7 | 55 | 6 | 2 |
| P8 | 60 | 6 | 3 |
| P9 | 60 | 6 | 2 |
| P10 | 60 | 6 | 2 |
| P11 | 48 | 6 | 0 |
| P12 | 46 | 9 | 7 |

Example 2

Solubility of Native Peptides and FCPs in Water

The solubility of each FCP in water was assessed. Each FCP was dispersed in 300 μl of water to a final concentration of 1.333 mM and vortexed and sonicated. The typical dispersion conditions were four sequences of three minutes bath sonication interspersed by 30 seconds vortexing. After inspection, the resulting solution was diluted with a mannitol solution (a candidate lyophilisation medium, final concentration of peptide 0.167 mM, 1.33% (w/v) mannitol). Solubility was assessed by visual observation of the cloudiness of the resulting dispersion (scaled: Clear/Cloudy−/Cloudy/Cloudy+) and presence of particulates. The results are shown in Table 2.

TABLE 2

FCP Dispersibility and Solubility in Water and 1.33% (w/v) Mannitol Solution

| Fluorocarbon-linked Peptide | Dispersion in Water Solubility | Further dilution in Mannitol:Water Solubility |
|---|---|---|
| FCP1 | Cloudy/Particulates | Clear/Particulates |
| FCP2 | Cloudy−/No Particulates | Clear/No Particulates |
| FCP3 | Cloudy−/Particulates | Clear/Particulates |
| FCP4 | Clear/No Particulates | Clear/No Particulates |
| FCP5 | Cloudy/Particulates | Cloudy−/Particulates |
| FCP6 | Cloudy−/Particulates | Clear/Particulates |
| FCP7 | Cloudy+/No Particulates | Cloudy+/No Particulates |
| FCP8 | Cloudy/Particulates | Cloudy/Particulates |
| FCP9 | Cloudy−/Particulates | Clear/Particulates |
| FCP10 | Cloudy−/Particulates | Clear/Particulates |
| FCP11 | Clear/No Particulates | Clear/No Particulates |
| FCP12 | Cloudy/Particulates | Cloudy−/Particulates |

Visual inspection of the individual fluorocarbon-linked peptide solution after the initial dispersion in water showed that only P4 and P11 were fully soluble in water; each of these solutions was clear with no presence of particulates. All the remaining solutions were cloudy and contained particulates, indicating that these FCPs were not fully soluble. On subsequent dilution with the mannitol solution, P2, P4 and P11 were fully soluble with clear solutions and no visible particulates. Solutions P1, P3, P6, P9 and P10 were also clear but particulates were observed, indicating that they were partially soluble in the mannitol\water solution. P5, P7, P8 and P12 were insoluble in the mannitol\water solution giving cloudy solutions containing particulates. Neither the percentage hydrophobicity of the peptide sequence or the positive or negative charges was found to correlate with solubility.

For comparison, native peptide solubility was also assessed in water at the same molecular concentration; for all native peptides except P8 the solutions were clear with no particulates visually detected.

In conclusion, the solubility of each Fluorocarbon-linked peptide is dependent upon its aggregation properties; the majority of the FCPs were not fully soluble in water or the mannitol solution. The solubility of each FCP could not be predicted from its physiochemical characteristics. The equivalent native peptides were more soluble in water than the FCPs at the same concentration.

The solubility of mixtures of the fluorocarbon-linked peptides was also assessed. Octavalent formulations (final concentration of each peptide 0.167 mM, 1.33% (w/v) mannitol, FCP compositions provided in Table 3) were prepared. The recovery of each peptide following sterile filtration (0.22 μm Millex 25 mm PVDF filter) was determined by RP-HPLC.

TABLE 3

Composition of Octavalent Mixtures of FCPs and Recoveries of Each FCP Following Sterile Filtration

| Fluorocarbon-linked Peptide | MIX 1 After Blending | YIELD % | Fluorocarbon-linked Peptide | MIX 2 After Blending | YIELD % |
|---|---|---|---|---|---|
| FCP1 | Cloudy with particulates | 89.9 | FCP10 | Cloudy with particulates | 90.7 |
| FCP4 | | 25.1 | FCP2 | | 97.3 |
| FCP5 | | 93.8 | FCP4 | | 82.3 |
| FCP6 | | 74.1 | FCP5 | | 35.6 |
| FCP7 | | 31.7 | FCP6 | | 8.8 |
| FCP3 | | 28.6 | FCP7 | | 63.2 |

TABLE 3-continued

Composition of Octavalent Mixtures of FCPs and Recoveries of Each FCP Following Sterile Filtration

| Fluoro-carbon-linked Peptide | MIX 1 After Blending | YIELD % | Fluoro-carbon-linked Peptide | MIX 2 After Blending | YIELD % |
|---|---|---|---|---|---|
| FCP9 | | 22.9 | FCP8 | | 25.3 |
| FCP12 | | 29.6 | FCP11 | | 49.4 |

The visual observations were confirmed by the HPLC filtration recovery results. The total RP-HPLC filtration recovery yields were approximately 50% and 57% for MIX 1 and MIX 2 respectively indicating that large particulates of FCPs were removed upon filtration. Mixtures of FCPs are therefore also poorly soluble in water.

Example 3

Solubility of FCPs in Excipients and Dispersants

In order to improve the solubility of fluorocarbon-linked peptides in water a range of excipients and dispersants, that have proved beneficial previously in pharmaceutical product manufacture, were evaluated. These included Polyethylene glycols, Pluronic surfactants, lecithin, glycerin, soybean oil, safflower oil, glycofurol, dipalmitoyl phosphatidylcholine, Labrafac CC (a medium-chain glyceride), hydroxylpropyl betacyclodextrin (HPBCD) and sulfobutyl ether beta-cyclodextrin and combinations thereof. The solubility of a heptavalent equimassic mixture of fluorocarbon-linked peptides was determined by microscopic inspection (final concentration 2.5 mg/ml).

None of the conditions tested was able to achieve a good dispersion of the fluorocarbon-linked peptides. HPBCD was found to improve the solubilisation but one day incubation at room temperature was needed to achieve 70-80% solubility. In conclusion, the fluorocarbon-linked peptides were resistant to the action of dispersants such as cyclodextrins, surfactants or block-copolymers.

Example 4

Solubility of FCPs in Organic Solvents

The solubility of fluorocarbon-linked peptides was assessed in a range of organic solvents. For 80% (v/v) propan-2-ol, tert-butanol, DMSO and acetone, solutions were prepared to the same fluorocarbon-linked peptide final concentration of 1.33 mM. For 80% (v/v) acetic acid the final concentration of the fluorocarbon-linked peptide was 2.0 mM. The results are presented in FIG. 3.

In conclusion, all fluorocarbon-linked peptides were soluble in 80% v/v acetic acid, with no foam or particulates observed. The 80% (v/v) propan-2-ol, tert-butanol, DMSO and acetone solutions were not able to provide complete solubility for the FCPs evaluated.

Example 5

Effects of Mannitol on Solubilisation

The effect of dilution and addition of mannitol on solubilisation in various solvents was investigated. Each fluorocarbon-linked peptide was dispersed in 80% v/v solvent in water according to the FIG. 4 and vortexed, followed by a seven-fold dilution with a mannitol-solution. For 80% v/v propan-2-ol, tert-butanol, DMSO and acetone solutions were prepared to the same fluorocarbon-linked peptide final concentration of 0.167 mM and a final mannitol concentration of 1.33% (w/v). For 80% v/v acetic acid the final concentration of the fluorocarbon-linked peptide was 0.25 mM. The results are presented in FIG. 4.

Equimolar mixtures of fluorocarbon-linked peptides were also prepared as above containing the following peptides in each solvent:

Mix 1: FCP1, FCP3, FCP4, FCP5, FCP6, FCP7, FCP9, FCP12.

Mix 2: FCP2, FCP4, FCP5, FCP6, FCP7, FCP8, FCP10, FCP11.

Effective solubility of the individual FCPs and Mix 1 and 2 was only achievable using 80% (v/v) acetic acid as presented in FIG. 4.

Example 6

Recovery of FCPs Following Sterile Filtration of FCP Solutions

The recovery following sterile filtration (0.22 μm Millex 25 mm PVDF filter) of each fluorocarbon-linked peptide in the mixtures prepared in Example 4 was determined by RP-HPLC. The results are shown in Tables 4 and 5 below.

TABLE 4

% Filtration Recoveries of Individual FCPs From Octavalent Mixture Mix 1

| Fluorocarbon-linked peptide | 80% v/v Acetic acid | 80% v/v Propan-2-ol | 80% v/v Tert-butanol | 80% v/v DMSO | 80% v/v Acetone |
|---|---|---|---|---|---|
| FCP1 | 100.2 | 97.8 | 96.1 | 95.1 | 89.9 |
| FCP12 | 100.2 | 16.9 | 6.6 | 32.0 | 12.7 |
| FCP3 | 100.5 | 97.9 | 102.0 | 100.8 | 99.6 |
| FCP4 | 99.8 | 20.5 | 19.3 | 77.2 | 24.4 |
| FCP7 | 99.4 | 90.9 | 99.9 | 47.8 | 42.7 |
| FCP9 | 99.8 | 84.3 | 84.9 | 87.7 | 69.1 |
| FCP5 | 100.2 | 34.3 | 90.2 | 17.2 | 3.2 |
| FCP6 | 101.3 | 78.4 | 62.3 | 85.8 | 63.2 |
| Mean | 100.2 | 65.1 | 70.2 | 67.9 | 50.6 |

TABLE 5

Percentage Filtration Recoveries of Individual FCPs From the Octavalent Mixture Mix 2

| Fluorocarbon-linked peptide | 80% v/v Acetic acid | 80% v/v Propan-2-ol | 80% v/v Tert-butanol | 80% v/v DMSO | 80% v/v Acetone |
|---|---|---|---|---|---|
| FCP11 | 99.5 | 57.4 | 52.3 | 85.4 | 76.4 |
| FCP2 | 99.8 | 92.7 | 99.5 | 98.2 | 85.4 |
| FCP4 | 100 | 21.6 | 10.0 | 73.0 | 4.5 |
| FCP7 | 93.3 | 90.5 | 89.2 | 46.4 | 43.7 |
| FCP8 | 99.8 | 20.7 | 21.2 | 34.9 | 17.6 |
| FCP10 | 98.1 | 87.7 | 87.3 | 89.4 | 79.4 |
| FCP5 | 99.1 | 35.9 | 51.8 | 18.1 | 2.9 |
| FCP6 | 97.4 | 69.5 | 82.1 | 91.0 | 64.1 |
| mean | 98.4 | 59.5 | 61.7 | 67.1 | 46.7 |

No loss of fluorocarbon-linked peptide was detected following sterile filtration for the mixtures prepared using 80% (v/v) acetic acid. It is concluded that acetic acid with subsequent aqueous dilution is the preferred solvent for the dissolution and filtration of fluorocarbon-linked peptides, but it will be necessary to reduce the concentration used in order to minimise the levels of residual acetic acid in the final product.

Example 7

Effect of Concentration of Acetic Acid on Solubility of FCPs

In order to limit the concentration of acetic acid downstream in the formulation process and in the final product, the lowest concentration of acetic acid in water to achieve efficient dispersion and maintain visible solubility was determined for each fluorocarbon-linked peptide. When using mannitol as a cryprotectant, it is important to minimize the acetic acid concentration at the lyophilisation stage in order to achieve a stable and amorphous freeze-dried product. The minimum acetic acid concentration to achieve acceptable dispersibility and solubility of the individual fluorocarbon-linked peptides was determined. The final concentration of fluorocarbon-linked peptide after initial acetic acid dispersion was 2 mmol/ml and after dilution with mannitol, 0.250 µmol/ml.

TABLE 6

Dispersibility and Solubility of Individual FCPs and a Heptavalent Mixture (Mix 3) in Acetic Acid

| Fluorocarbon-linked peptide | Percentage acetic acid (% v/v) | Ease of dispersion by sonication/ vortexing | Visual appearance after dispersion | Visual appearance of mixture after dispersion: Mix 3 |
|---|---|---|---|---|
| FCP1 | 10 | +++ | Clear | Clear |
| FCP2 | 10 | +++ | Clear | |
| FCP4 | 10 | +++ | Clear | |
| FCP8 | 80 | + | Clear | |
| FCP9 | 80 | + | Clear | |
| FCP5 | 10 | +++ | Clear | |
| FCP6 | 80 | + | Clear | |

A concentration of acetic acid as low as 10% v/v was found to provide adequate dispersion for several of the fluorocarbon-linked peptides. However, whilst some fluorocarbon-linked peptides required less than 80% (v/v) acetic to achieve full dissolution, the resulting formulation proved to be physically unstable over time with a gel or soluble particulates being formed (for example FCP6, FCP8 and FCP9). For these three peptides, 80% (v/v) acetic acid was found to achieve complete dispersion while preventing any change in physical state.

Filtration recovery was measured by RP-HPLC comparing peak areas of each fluorocarbon-linked peptide within the Mix 3 mixture before and after sterile filtration. The percentage recovery was measured for each FCP and a mean recovery calculated as an average of the percentage of recovery of each individual FCP. The overall filtration recoveries (based on 0.22 µm filter) measured after blending and dilution were typically greater than 95%.

TABLE 7

Filtration Recovery

| FCP | Filtration recovery |
|---|---|
| FCP1 | 100.0 |
| FCP2 | 99.3 |
| FCP4 | 98.6 |

TABLE 7-continued

Filtration Recovery

| FCP | Filtration recovery |
|---|---|
| FCP5 | 98.7 |
| FCP6 | 100.0 |
| FCP8 | 97.0 |
| FCP9 | 95.4 |
| Mean | 98.4 |

Example 8

Characterisation of Structures Formed by Fluorocarbon-Linked Peptides

The formation of self-assembled multimolecular micellar structures may play a central role in the solubilisation process of fluorocarbon-linked peptides. In this manner, the solubility of fluorocarbon-linked peptides can be maintained following dispersion and subsequently throughout the formulation process, particularly in the reconstitution of the lyophilised product. The physical characterisation of the multimolecular structures assembled during dispersion was performed using Dynamic Light Scattering (DLS) and Transmission Electron Microscopy (TEM).

A Zetasizer Nano S (enabling measurement of particles from 0.6 nm to 6 microns) was employed to monitor the particle size of a mixture of fluorocarbon-linked peptides based on DLS. Mix 1 (FCP1, FCP3, FCP4, FCP5, FCP6, FCP7, FCP9 and FCP12) was prepared as described in Example 1 (Table 3) with mannitol diluent.

The average particle size (nm) of each mixture was measured at 25° C. using a Nanosizer (Zetasizer Nano Series ZS, Malvern Instruments, UK). 250 µl of solution was used and dispatched in a plastic microcuvette. Correlation times were based on 10 s per run and a total of 5 runs per measurement were made. Results were analysed using Dispersion Technology Software (Malvern Instruments, UK). Size distribution by volume and in intensity was obtained for Mix 1. Average size based volumetric measurement was calculated by the Dispersion Technology Software.

Figure 5:
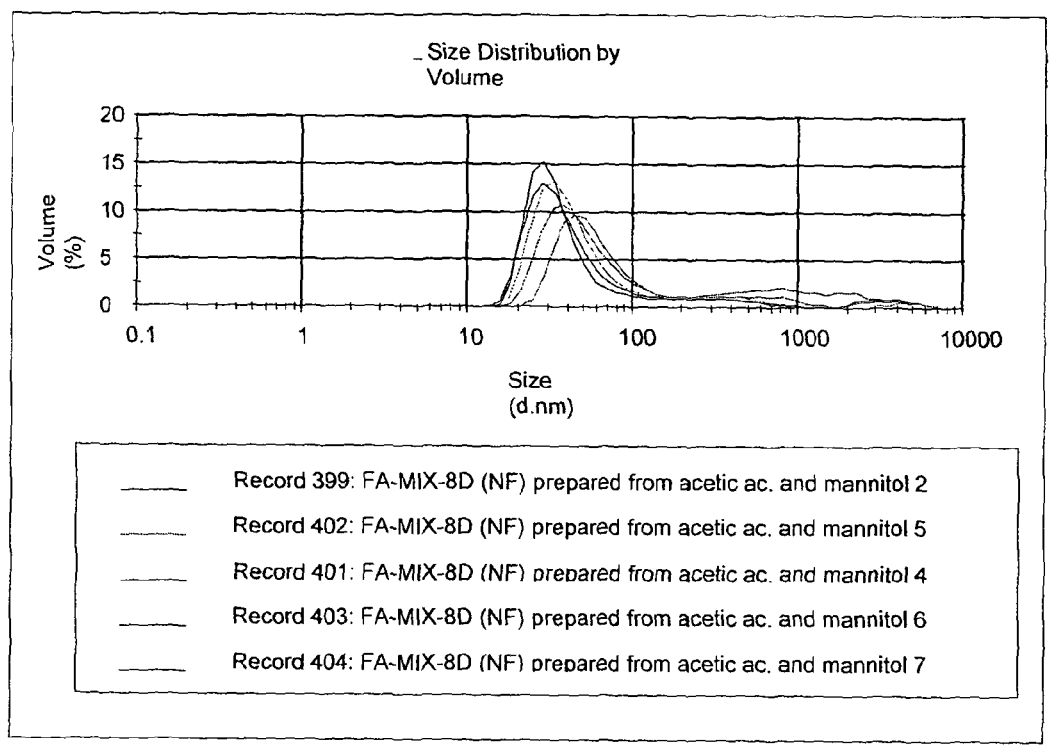
FIG. 5 shows the particle size of fluorocarbon-linked peptides in solution post-blending and dilution assessed by Dynamic Light Scattering (DLS).

The DLS of fluorocarbon-linked peptides in solution demonstrates the presence of multimolecular structures of diameter centred around 20 to 50 nm (>95% by volume) with approximately 12-16% (by intensity) of the population with a size greater than 100 nm (FIG. 5).

Figure 6:
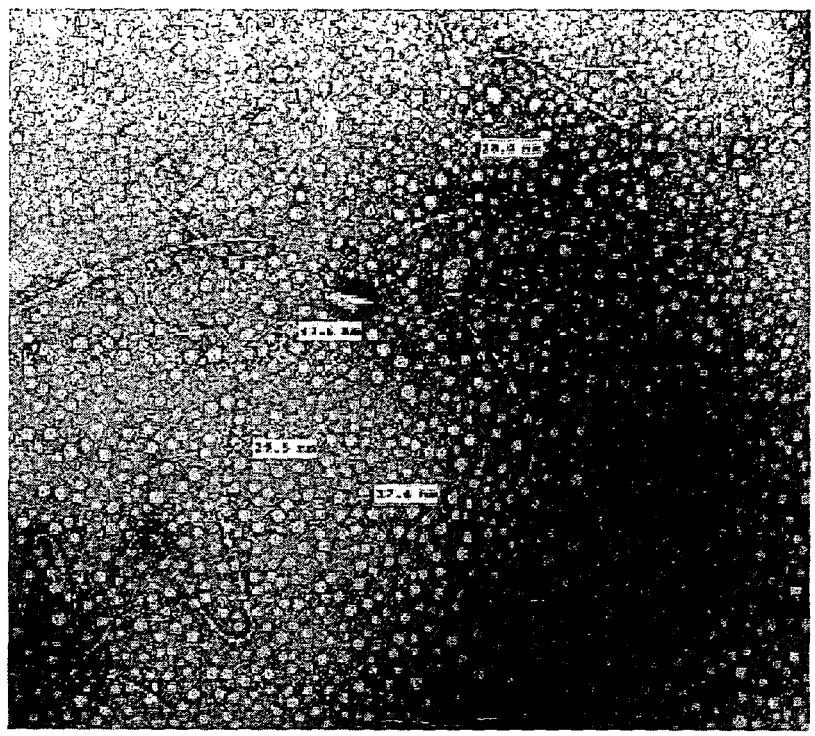
FIG. 6 shows the size and shape of fluorocarbon-linked peptide particles in solution post-blending and dilution assessed by transmission electron microscopy (TEM).

TEM showed the presence of a homogenous population of spherical structures of dimensions consistent with the DLS (FIG. 6).

Example 9

Impact of Sterilising Grade Filtration on Multimolecular FCP Structures

The impact of sterilising grade filtration upon the multimolecular structures was investigated. Mix 1 from Example 7 was filtered via a sterile 0.22 nm Millex 25 mm PVDF filter and then analysed by DLS using a Zetasizer Nano S as described in Example 7.

DLS analysis demonstrated that the structures formed are highly dynamic with variable reproducibility even within the one set of analysis. Between five and seven measurements were collected to calculate the average particle size (represented by the different profiles in FIG. 7).

Surprisingly, it was found that the 0.22 μm filtration may re-shape the multimolecular structures formed by fluorocarbon-linked peptides initially solubilised in acetic acid. DLS shows that large particles are re-shaped into smaller particles post-filtration and that the Kcount (a parameter that correlates with the number of particles in solution) is also drastically reduced post-filtration (pre-filtration, 200 Kcounts; after post-filtration, 120 Kcounts). Moreover, the introduction of a 0.45 μm filter ahead of the 0.22 μm filter did not reduce filtration recoveries. Sterilising grade filtration can therefore influence the resulting size of the structures assembled, not by simply removing large particles from the formulation and restricting their passage downstream of the manufacturing process (with a concomitant reduction in yield), but rather by re-shaping the structures by deformation so they are able to pass through the filter. Particles with size over 220 nm represent around 12 to 16% (by intensity) of the particles in the mixture, according to the DLS data. These would appear not to be removed from the solution as the filtration recovery determined by HPLC is over 97%.

Figure 8:
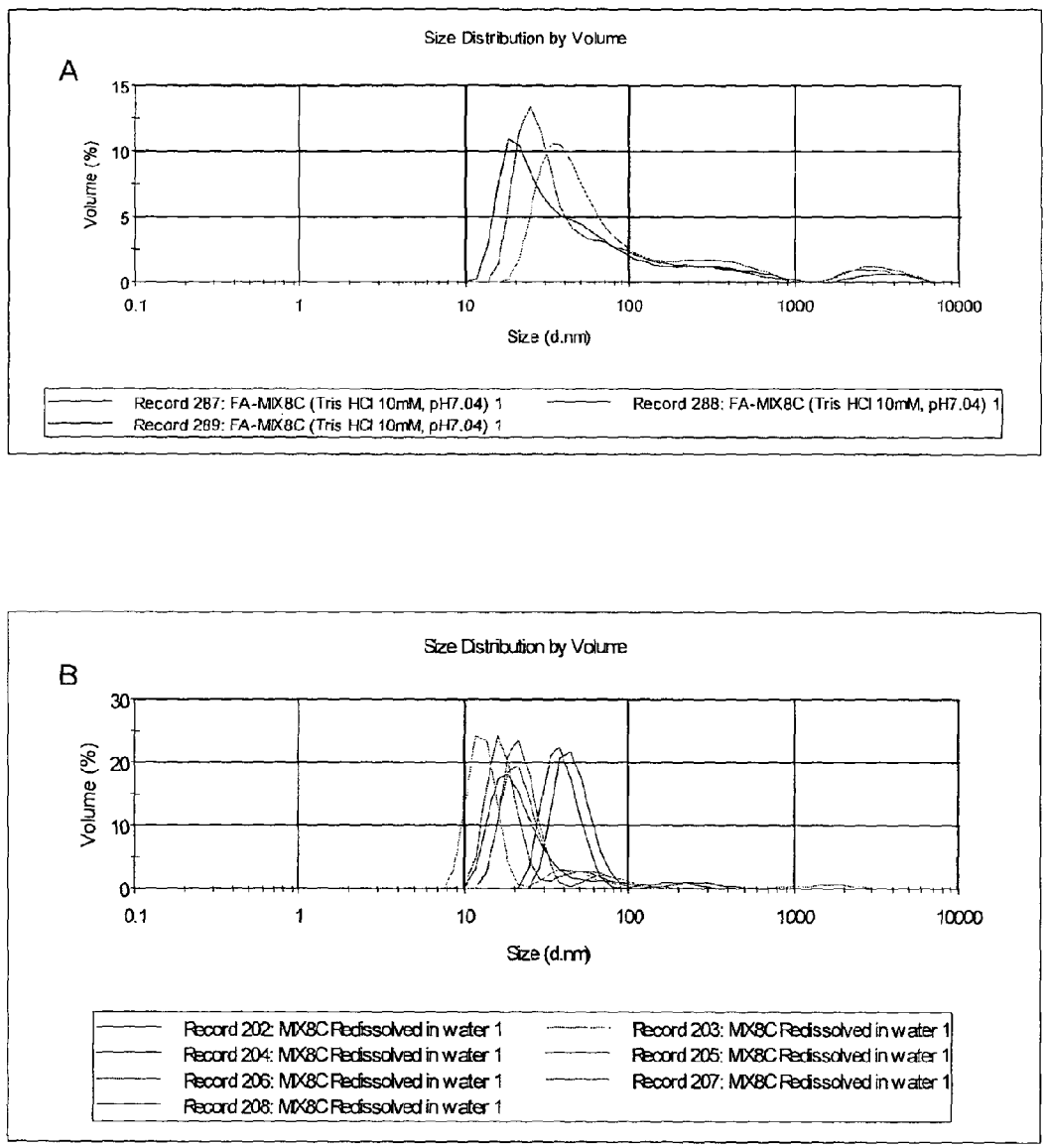
FIG. 8 shows the size distributions by volume of fluorocarbon-linked peptide particles reconstituted in Tris 10 mM pH 7.85 (A) and water (B) assessed by DLS.

The MIX 1 formulation particle size distribution was also assessed after freeze-drying following reconstitution of samples in Tris-HCl 10 mM or water (FIG. 8). The MIX 1 formulation was readily reconstituted achieving a clear or slightly opalescent solution with water or Tris-HCl 10 mM respectively. Particle sizes were centered around 20-50 nM with a profile broadly similar to that observed during formulation (pre-lyophilisation). This demonstrates that post-reconstitution; FCPs multimolecular structures are maintained without the formation of large visible aggregates.

Example 10

Chemical Stability of FCPs

The chemical stability of the fluorocarbon-linked peptides was assessed by exposing a lyophilised formulation of seven fluorocarbon-linked peptides to 50% (v/v) acetic acid for 24 hours. Mix 3 was prepared by initial solubilisation of the FCPs in acetic acid (concentration of solvent for each FCP as given in Example 6), followed by dilution and blending with a mannitol solution. The mixture was then lyophilised prior to reconstitution in 50% (v/v) acetic acid.

Figure 9:
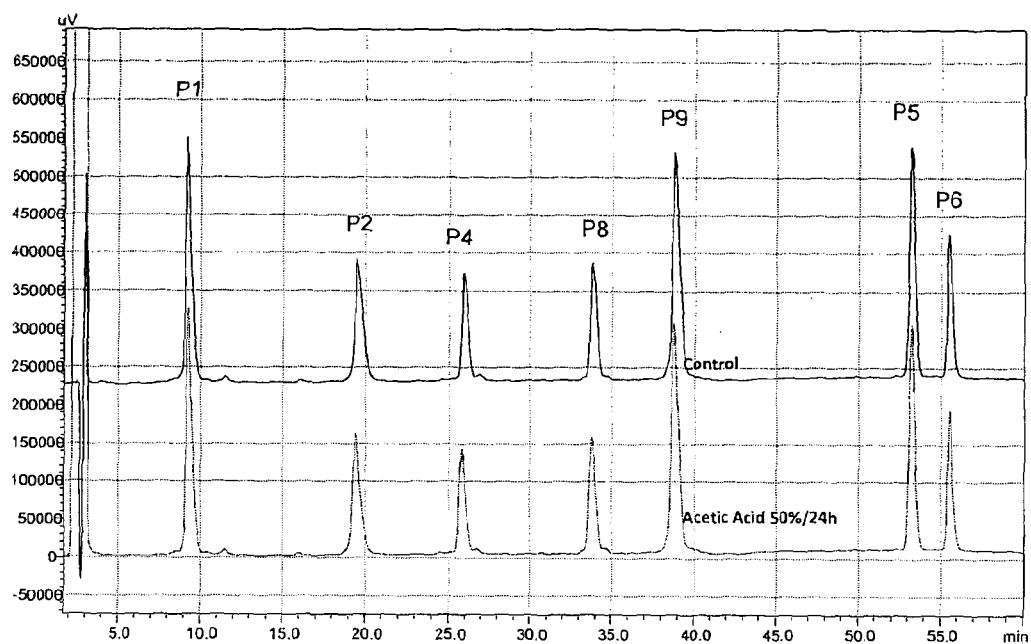
FIG. 9 shows the results of RP-HPLC analysis of a mixture of seven fluorocarbon-linked peptides exposed to 50% (v/v) acetic acid for 24 hours.

No degradation was observed by RP-HPLC compared to an untreated control (see FIG. 9). This demonstrated that the selected fluorocarbon-linked peptides are chemically stable in 50% v/v acetic acid for the duration of a typical blending step during a pharmaceutical manufacturing process.

Example 11

Residual Acetate Concentration in Final Presentation

It is important to minimise the acetic acid concentration in the downstream formulation. This will allow the formation of a stable cake during lyophilisation and raise the pH of the preparation closer to the desired neutrality. Acetic acid is volatile and its content thereby reduced during the freeze-drying process.

For lyophilisation, formulations of Mix 3 prepared as described in Example 9 (3 ml freeze-drying vials filled with 1.4 ml volume) were firstly frozen for two hours in an −80° C. freezer and then freeze-dried (benchtop Christ Alpha2-4 LSC) for 24 hours. This procedure allowed the production of lyophilised cakes with a stable structure and homogenous consistency. The pre-lyophilisation concentration of acetate in the formulation was calculated to be 8.8% v/v.

For three different batches, the post-lyophilisation residual acetate concentration (acetate counterions plus acetic acid) in the vials was experimentally determined to be 0.3-0.4, 0.7 and 0.5% (w/w) respectively. The standard deviation of this analysis was validated as +/−0.07% (w/w) for acetate; the limit of quantitation as 0.1% (w/w). The mean value of residual acetate equates to an acceptable level of approximately 0.35 mg per human dose, well below the ICH recommendation (maximum 50 mg per day).

Example 12

Reconstitution of Lyophilised FCP Preparations

The reconstitution of formulated fluorocarbon-linked peptides (Heptavalent, Mix 3) was compared to an unformulated equivalent preparation. The individual FCPs were solubilised in acetic acid as described in Example 9, blended and diluted with a mannitol solution and lyophilised (final concentration 0.35 mg per FCP). One vial of the formulated mixture was reconstituted with 0.7 ml of Water for Injection (Hyclone); an additional vial was reconstituted with 0.7 ml of 28 mM histidine buffer solution. For the unformulated mixture 0.35 mg of each, untreated, FCP was dispensed into a vial with no additional processing. One vial of the unformulated mixture was reconstituted with 0.7 ml of 4.5% mannitol solution to provide an identical excipient concentration to that of the formulated vials. An additional vial of the unformulated mixture was reconstituted with 0.7 ml of 28 mM histidine in 4.5% mannitol solution.

Figure 10:
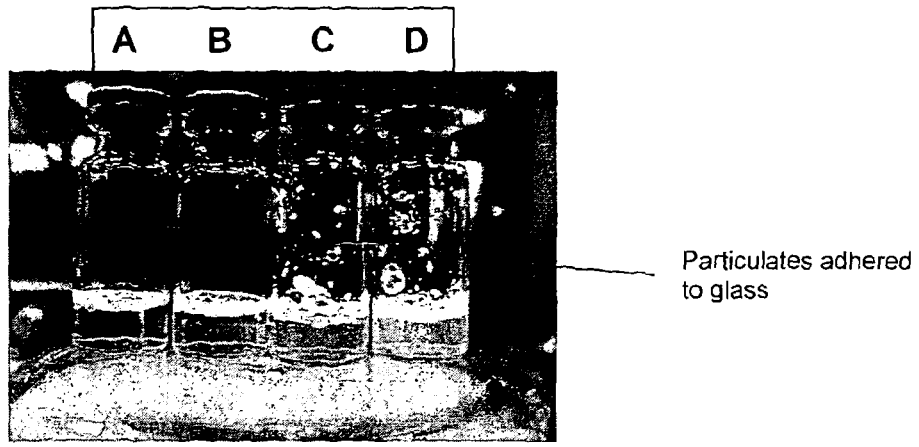
FIG. 10 shows photographs of formulated and unformulated mixtures of fluorocarbon-linked peptides after being shaken by hand. Vial A: formulated+mannitol/water; Vial B: formulated+mannitol/histidine; Vial C: non-formulated+mannitol/water; Vial D: non-formulated+mannitol/histidine.
Figure 11:
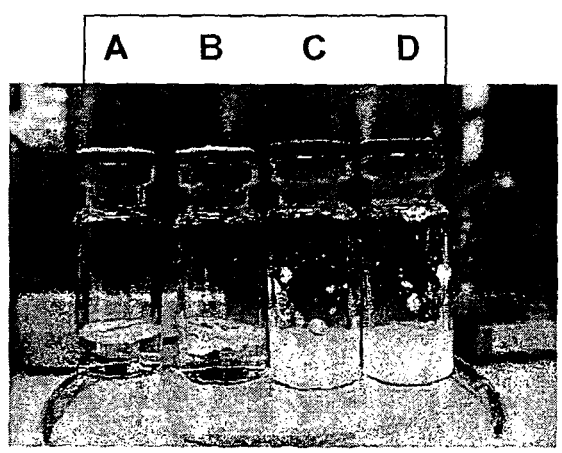
FIG. 11 shows photographs of formulated and unformulated mixtures of fluorocarbon-linked peptides after being vortexed and sonicated. Vial A: formulated+mannitol/water; Vial B: formulated+mannitol/histidine; Vial C: non-formulated+mannitol/water; Vial D: non-formulated+mannitol/histidine.

The photographs below (FIGS. 10 and 11) illustrate the solubility of the FCPs following initial dispersion by manual shaking and subsequent vortexing for 30 seconds and bath sonication for a period of one hour.

Visual inspection of the unformulated samples after reconstitution with both the mannitol/water and histidine buffer solutions showed that the solutions were not fully dispersed and solubilised. Each solution was cloudy and large particulates could be observed, in particular adhering to the side of the glass vial, which did not disperse over time. In contrast, the solutions of the formulated vaccine dispersed in both the water and histidine buffer solutions were clear with no presence of particulates.

These results demonstrate that the method of initial solubilisation has an impact upon the aggregative properties of the final reconstituted formulation. Dispersion of the FCP in acetic acid early in the formulation process directs the formation of micellar structures, which are maintained through the subsequent blending, filtration and lyophilisation processes. This facilitates the reconstitution of the final lyophilised presentation in an aqueous phase in a non-particulate form.

CONCLUSIONS

Acetic acid was demonstrated to be a good solvent for all individual fluorocarbon-linked peptides evaluated. Complete solubilisation was achievable at high FCP concentrations (up to 2000 nmol/ml; approximately 10 mg/ml) with no particulates observed following perturbation by vortexing and sonication. Solubility was maintained during further downstream processing due to the amphiphilic properties of fluorocarbon-linked peptides directing the formation of spontaneously self-assembled macromolecular structures as observed by Dynamic light scattering and transmission electron microscopy. The solvent is therefore contributing a dual role; firstly in ensuring that there is sufficient disruptive capability to ensure that large disordered particulate structures are disrupted and secondly supporting an environment whereby multimolecular, ordered, micellar structures may be created and supported. These structures are small enough to allow solubilisation of the FCP such that no loss of material occurs upon sterile filtration. The micellar structures are also retained during lyophilisation and are essential to facilitate the resolubilisation of the lyophilisate in an aqueous media prior to administration to humans. FCPs that had not been previously solubilised in acetic acid could not be satisfactorily reconstituted from a freeze-dried state in water or histidine buffer (Example 12).

80% (v/v) acetic acid was found to solubilise all FCPs. However, excessive acetic acid can prevent the formation of an acceptable lyophilisate cake following freeze-drying. In addition, there are regulatory constraints imposed upon the levels of acetate in pharmaceutical products. Lower concentrations of acetic acid were therefore examined; with 10% (v/v) proving to be suitable for four of the seven FCPs, whilst 80% (v/v) was the lowest concentration viable for the remaining three FCPs. On processing, this blend of seven FCPs produced an acceptable lyophilisate cake with compliant levels of acetate per human dose.

All other solvents investigated were unable to achieve complete solubilisation of all the FCPs. The success of acetic acid was not predictable, as the fluorocarbon chain imparts unusual physicochemical properties upon the molecule (compare for example, the solubilities of the FCPs and the equivalent native peptides in Example 1). In addition, there was no correlation between the success of 10% (v/v) acetic acid in solubilising an FCP and the hydrophobicity or charged residue content of the peptide.

In summary, acetic acid has the following advantages:

capable of providing adequate solubility for not only the individual FCPs but also mixtures thereof;
suitable for all FCPs evaluated;
Yields consistent and uniform products;
Water-miscible at the concentrations intended for use (10-80% (v/v);
Able to solubilise the FCPs at relatively high concentrations (at least 10 millimolar);
Listed as a ICH class III solvent, suitable for human use;
Amenable to lyophilisation (with levels being reduced after a typical freeze-drying stage);
Results, after subsequent blending and dilution, in a solution that van be subjected to sterilising grade filtration with minimal yield losses;
Results, after lyophilisation, in a product that can be readily reconstituted to form an isotonic, pH neutral, homogeneous suspension;
Does not react with, or promote degradation of, the fluorocarbon-linked peptide; and
Compatible with the materials routinely used in pharmaceutical product manufacture.

Example 13

Preparation of a Fluorocarbon-Linked Peptide Influenza Vaccine

The objective of this study is to demonstrate the benefit of a formulation process designed for the good manufacturing practice (GMP) production of a pharmaceutically acceptable universal influenza-A vaccine (FP01.1) containing six fluoropeptides, which comprises peptides with the amino acid sequences shown in SEQ ID NOs: 1 to 6. The specific objectives are:
1. To assess key formulation parameters for the manufacture of FP-01.1.
   a. Ease of fluoropeptide solubilisation in acetic acid solutions;
   b. Micelle size determination at the point of filtration;
   c. Filtration recovery;
   d. Chemical and physical stability of the fluoropeptides; and
2. To compare the quality of the reconstituted FP-01.1 vaccine (formulated fluoropeptides) with an equivalent preparation containing non-formulated fluoropeptides.

We have developed a formulation process and applied it to the manufacture of a universal influenza-A vaccine FP-01.1 composed of six fluorocarbon-linked peptides comprising SEQ ID NOs: 1 to 6, respectively. The six peptides having the sequences shown in SEQ ID NOs: 1 to 6 are coupled to the fluorocarbon chain $C_8F_{17}(CH_2)_2COOH$ via the epsilon chain of an N-terminal lysine spacer. The six fluorocarbon-linked peptides thus correspond to FCP1, FCP8, FCP9, FCP2, FCP4 and FCP5 described in the preceding Examples. The formulation process is based on the use of acetic acid, an acidic solvent that we have found ensures good dispersability of the fluoropeptides whilst maintaining physical and chemical stability of the fluoropeptides during the process. Acetic acid is highly volatile and can be sublimated during freeze-drying and we have found that it is consistently reduced to residual levels that have little impact on the pH of the reconstituted product.

The formulation process described below achieves the manufacture of a freeze-dried FP01.1 vaccine (ensuring long term stability) to be reconstituted with a buffer solution (28 mM L-Histidine) to generate a stable homogenous solution (no visible aggregates) with neutral pH (6-7.5) and acceptable osmolality (280-320 mOsm). Several GMP clinical batches have been usefully produced and we have demonstrated that the product is safe and immunogenic in humans.

Materials and Instruments
Fluoropeptides (contained in FP-01.1) manufactured by the American Peptide Company
Glacial acetic acid (Sigma#27225), D-Mannitol (Merck Emprove)
Hyclone water (Fisher#HYC-001-189G)
Millex, PVDF Durapore, 0.2 μm (ø33 mm) Millipore.
30 Autoclaved (Freeze dried vials (Adelphi#VC002-13C)+stoppers (Adelphi#FDW13)).
HPLC equipped with Discovery Column C18, 250×2.1 mm, 5 μm
Combitips pipette tips 10 ml (Fisher#PMP-117-523N)+Eppendorf Stepper
Freeze drier 2-4-LSC (Christ)
Osmomater:Osmomat 030 (Gonotec)
pH meter equipped with micro Inlab® electrode (Mettler)

Methods

Solution Preparation 1. 3.3% w/w Mannitol in 50 ml in water (6.6 g in 200 ml water), cool down at 4° C.
2. 5 ml solutions of acetic acid at 10% (v/v) in sterile water.
3. 5 ml solutions of acetic acid at 80% (v/v) in sterile water.

Fluorocarbon-Linked Peptide Weighing

TABLE 8

FCPs weighing and dispersion

| FCP | Mass (mg) (net) | Peptide content (%) | Mass (mg) Theoret. (gross) | Mass (mg) Experim. | Acetic Acid Conc (%) | Vol (µl) of acetic acid-Theoret. | Vol (µl) of acetic acid-Exper. |
|---|---|---|---|---|---|---|---|
| FCP1 | 10 | 87.0 | 11.49 | 12.27 | 10 | 1000 | 1068 |
| FCP2 | 10 | 87.6 | 11.41 | 12.49 | 10 | 1000 | 1094 |
| FCP4 | 10 | 90.6 | 11.04 | 11.68 | 10 | 1000 | 1058 |
| FCP5 | 10 | 92.0 | 10.87 | 11.67 | 10 | 1000 | 1074 |
| FCP9 | 10 | 90.3 | 11.07 | 11.60 | 80 | 1000 | 1048 |
| FCP8 | 10 | 92.0 | 10.87 | 11.78 | 80 | 1000 | 1084 |

Formulation Preparation for FP-01.1

1. Weigh each peptide (targeting 10 mg net peptide) in a 2 ml glass vial
2. Disperse each fluoropeptides at 10 mg net/ml in ~1.0 ml (adjust volumes in function of weighing to get exactly 10 mg net/ml) of 10% or 80% acetic acid solution in water (see table 10),
3. Vortex and sonicate and record visual aspect
4. Repeat step 3 until complete dissolution
5. Blend together 9500 of each of the 6 dispersed fluoropeptides into a 40 ml glass container. Then add 950 µl of acetic acid 80% (6.65 ml total volume). Each peptide is at a concentration of 1.428 mg/ml in 40% acetic acid.
6. Record visual aspect of the blended solution
7. Dilute the blended fluoropeptides with 25.93 ml of 3.3% mannitol (solution at 0.2915 mg/ml of each peptide), total acetic acid 8.16%.
8. Record visual aspect of the diluted solution
9. Filter the ~32 ml solution with a Millex PVDF 33 mm, 0.2 µm (keeping 0.3 ml unfiltered solution for filtration recovery).

Filling

Aliquot labelled 2 ml freeze according to Table 9 (Filling volume: 1.2 ml for each formulation), using 10 ml combitips.

TABLE 9

Preparation of Fluoropeptides formulation FP-01.1

| Total Volume (ml) | Peptide conc. (mg/pept/ml) | Aliquot for Lyo-philisat (µl) | Peptide quantity (µg/vial/peptide) | Buffer Vol. for reconstitution (µl) | Final concentration after reconstitution |
|---|---|---|---|---|---|
| 29-30 | 0.2915/ind | 1200 (24-25 vials) | 350 | 700 | 0.500 mg/pept/ml |

Freeze Drying

1. Freeze the vials at −80° C. for one hour.
2. Freeze dry for 40 hours
3. Freeze drying ventilation is performed under nitrogen and the vials stoppering is carried out at a pressure between 400 and 600 mbar.

Preparation of FP-01.1-Equivalent Using Non-Formulated Fluoropeptides

Two vials were prepared containing 0.35 mg of each of the 6 fluoropeptides: FCP1, FCP8, FCP9, FCP2, FCP4 and FCPS.

Transmission Electron Microscopy

TEM in negative staining, 20 µl of fluorocarbon-linked peptide solution is deposited on a Formvar carbon coated copper electron microscope grid (300 mesh). 20 µl of uranyle acetate (1% aqueous) is then added. After 30 seconds, excess solution is quickly wicked away with a Whatman filter paper. The sample is then allowed to dry for at least 2 minutes before analysis. Transmission electron microscopy is then performed on Philips CM120 biotwin at 120 kV accelerating voltage. Image acquisition is performed at a direct magnification ranging from 50000× to 150000×.

RP-HPLC Analysis

HPLC Method: FP-01.1

Column: Discovery C18: 2.1×25 mm, 5 µm, Flow 0.3 ml/min.

Solvent A: 90% water/10% acetonitrile/0.04% TFA

Solvent B: 90% acetonitrile 10% water 0.04% TFA).

Gradient:

| Time (min) | Solvent B |
|---|---|
| 0.01 | 10% |
| 1 | 10% |
| 6 | 28% |
| 46 | 44% |
| 50 | 57% |
| 60 | 70% |
| 68 | 82% |
| 70 | 82% |
| 71 | 10% |

Results
Formulation Step (Before Freeze Drying)
Peptide Dispersion

TABLE 10

Ease of solubility of each peptide after vortex/sonication cycle

| | Cycle 1 | | Cycle 2 | | Cycle 3 | |
|---|---|---|---|---|---|---|
| FCP | Vortexing | Sonication | Vortexing | Sonication | Vortexing | Sonication |
| FCP1 | Clear | Clear | Clear | Clear | Clear | Clear |
| FCP2 | Clear | Clear | Clear | Clear | Clear | Clear |
| FCP4 | Clear | Clear | Clear | Clear | Clear | Clear |
| FCP5 | Clear | Clear | Clear | Clear | Clear | Clear |
| FCP9 | Particulates− | Clear | Clear | Clear | Clear | Clear |
| FCP8 | Particulates+ | Some particulates | Some particulates | 1 or 2 particulates | 1 or 2 particulates | Clear |

Peptides were easily soluble with no sonication required, whereas the two peptides soluble in acetic acid 80% required at least 1 cycle of sonication.

Blending/Dilution

The solution of the 6 peptides blended was clear (no visible aggregates). Once diluted with the mannitol at 3.3%, the solution was still clear (no visible aggregates).

TABLE 11

Visual Appearances of Preparations

| Peptide | Percentage acetic acid (% v/v) | Ease of dispersion (see Table 12) | Visual appearance after dispersion | Visual appearance of mixture after blending | Visual appearance of mixture after Dilution |
|---|---|---|---|---|---|
| FCP1 | AcOH 10% | +++ | Clear | Clear | Clear |
| FCP2 | AcOH 10% | +++ | Clear | | |
| FCP4 | AcOH 10% | +++ | Clear | | |
| FCP5 | AcOH 10% | +++ | Clear | | |
| FCP9 | AcOH 80% | ++ | Clear | | |
| FCP8 | AcOH 80% | + | Clear | | |

Filtration Recoveries

Very good filtration recoveries were achieved (>99% for each peptide).

TABLE 12

Peptide recoveries after filtration

| | FCP | | | | | |
|---|---|---|---|---|---|---|
| | FCP1 | FCP2 | FCP4 | FCP5 | FCP9 | FCP8 |
| Peptide recovery % | 100.2 | 101.6 | 100.8 | 100.2 | 99.8 | 99.6 |

Transmission Electron Microscopy (TEM) Imaging

Figure 12:
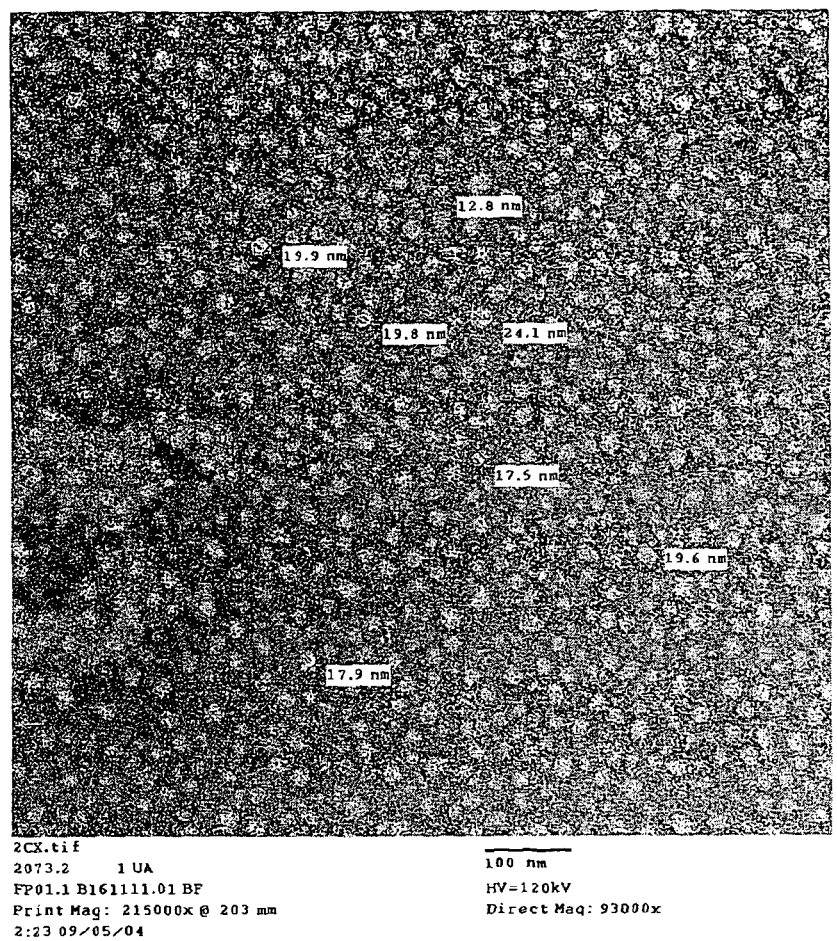
FIG. 12 shows transmission electron micrographs of a formulation comprising six fluorocarbon-linked influenza peptides (FP-01.1).

TEM analysis of the micelles formed before filtration shows the presence of a homogenous population of small spherical micelles with a size ranging from 17-30 nm (FIG. 12).

Chemical Stability (Post-Filtration)

Figure 13:
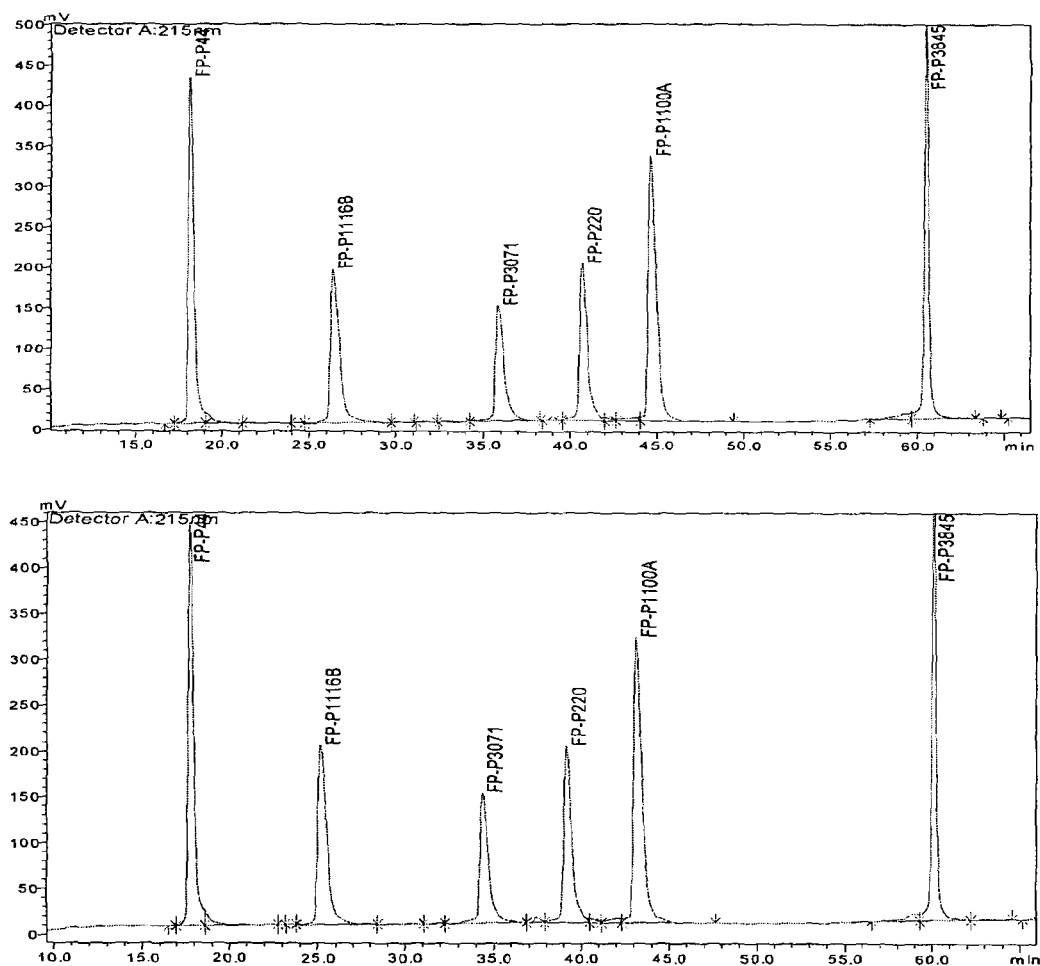
FIG. 13 shows the HPLC profile of post-filtered FR01.1 at to (upper panel) and after 24 hours (lower panel).

Chemical stability was determined by RP-HPLC at $T_0$ and after 24 hours post-filtration. The results are shown in FIG. 13 and Table 13.

TABLE 13

Post-filtration purities over time

| | T0 | 2 hrs | 8 hrs | 24 hrs |
|---|---|---|---|---|
| Purity % | 96.9 | 97.1 | 97.1 | 96.9 |
| HPLC file | 8644 | 8645 | 8649 | 8651 |

Analysis Performed on Finished FP-01.1 Product (Post-Freeze-Drying)

Cake Aspect after Freeze Drying

TABLE 14

Cake inspection results

| Product | Elegant cake | Collapsed cake | Total vials |
|---|---|---|---|
| FP01.1 | 25 | 0 | 25 |

The freeze-dried product forms an elegant solid uniform cake.

Purity Analysis of Freeze-dried FP-01.1 Product

A sample was reconstituted in 0.70 ml water to get a concentration at 0.5 mg/peptide. No degradation occurred during the freeze drying, with the purity of 97%.

Reconstitution of Freeze-Dried FP-01.1—Comparison with Unformulated Fluoropeptides To demonstrate the benefit of the formulation process applied to the production of FP-01.1, the quality of the reconstituted FP-01.1 vaccine (formulated fluoropeptides) was compared with an equivalent preparation containing non-formulated fluoropeptides.

Figure 14:
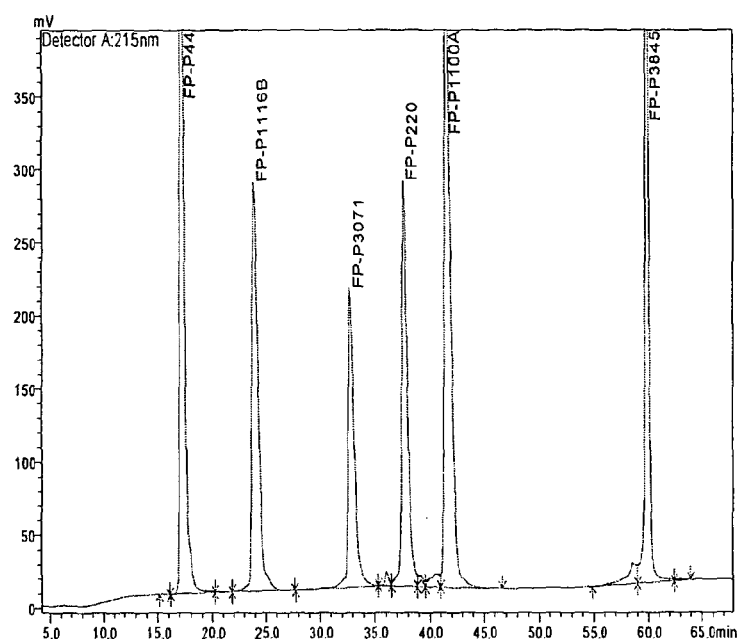
FIG. 14 shows the HPLC profile of FP01.1 after reconstitution in water.

The FP-01.1-equivalent based on non-formulated fluoropeptides was prepared by weighing the 6 fluoropeptides in a single vial (0.35 mg of each peptide). The non-formulated FP-01.1-equivalent was reconstituted with either 0.7 ml of water (containing 4.5% mannitol to be equivalent to FP-01.1) or 28 mM L-Histidine (containing 4.5% mannitol) and compared with the formulated FP-01.1 (obtained through the formulation process described above) and reconstituted under the same conditions. The reconstituted formulated FP01.1 was analysed by RP-HPLC and the results of the analysis are shown in FIG. 14.

Figure 15:
FIG. 15 shows a comparison of reconstituted formulated fluorocarbon peptides (FP01.1) and non-formulated peptides in water. The left photograph was taken after 20 minutes standing and the right photograph was taken after 3 minutes sonication.

The formulated FP-01.1 product was easily reconstituted in water while the non-formulated FP-01.1 equivalent is insoluble with large aggregates in suspension and adhering to the glass wall (see FIG. 15). FP-01.1 reconstituted in water lead to a very slightly opalescent homogeneous solution with no visible aggregates. The non-formulated fluoropeptides do not achieve solubility over time and even after sonication and vortexing.

Figure 16:
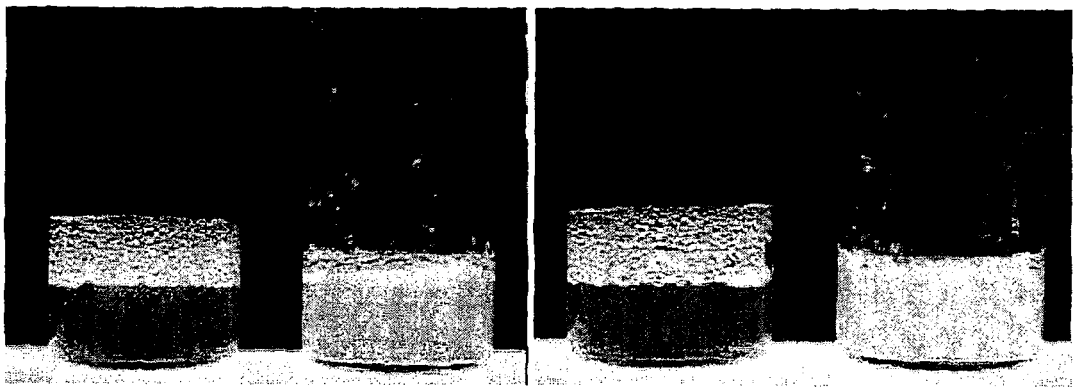
FIG. 16 shows a comparison of reconstituted formulated fluorocarbon peptides (FP01.1) and non-formulated peptides in 28 mM L-Histidine. The left photograph was taken after 20 minutes standing and the right photograph was taken after 3 minutes sonication.

Similarly, the formulated FP-01.1 product was easily reconstituted in 28 mM L-Histidine (buffer designed for the clinical product to achieve neutral pH) while the non-formulated peptides are insoluble (formation of large aggregates) (see FIG. 16). FP-01.1 reconstituted in water lead to a slightly opalescent homogeneous solution with no visible aggregates. The non-formulated fluoropeptides do not achieve solubility over time even after sonication and vortexing.

Based on these results, a product based on the non-formulated fluoropeptides would not be considered to be pharmaceutically acceptable due to its poor dispersability and the absence of homogeneity of the preparation.

Osmolality and pH of the Formulation in L-Histidine

TABLE 15 pH and osmolality of the reconstituted formulation in L-Histidine

|  | FP-01.1 reconstituted in Histidine 28 mM |
|---|---|
| Osmolality (mOsm/kg) | 302 |
| pH | 6.65 |

Conclusions

- All fluoropeptides achieved full solubility at the point of dispersion.
- Micelles were formed with a size ranging from 17 to 30 nm compatible with sterile filtration (220 nm cut-off).
- Sterile Filtration recovery was over 99% for all fluoropeptides.
- FP-01.1 was easily reconstituted with its dedicated 28 mM L-histidine buffer systems leading to a homogenous slightly opalescent solution with close to neutral pH and acceptable osmolality (~300 mOsm).
- An FP-01.1-equivalent preparation obtained from non-formulated fluoropeptides was demonstrated to be difficult to reconstitute with fluoropeptides forming large insoluble aggregates with a large proportion adhering to the glass wall. This contrast with the reconstitution of a formulated FP-01.1 and demonstrate the benefit of the formulation process in generating a pharmaceutically acceptable product.

Example 14

Immunogenicity of FP01.1 in Rats

The immune response that can be generated by the FP-01.1 formulation was assessed in rats were immunised intramuscularly on the lower left flank by staff members of the CBS, St Mary's Campus, Imperial College according to GD_RD004.

Preparation of Splenocytes

Rats were sacrificed according to home office regulations and GD_RD004.

Spleens were harvested (any abnormal spleens were photographed) and single cell suspensions were prepared according to GD_RD007, with cell numbers determined as described in GD_RD001 (TruCount Method). Splenocytes were resuspended to $1\times10$/mL in complete media and plated for IFNγ ELISpot and CBA.

IFNγELISpot

Antigens for stimulation were freshly prepared at 4× concentration from stocks and plated in duplicate wells for IFNγ ELISPOT. Cells were plated at $0.5\times10^6$ splenocytes/well (50 μL of cell suspension), with 50 μL of 4× antigen preparation (i.e. individual long peptides and LPMIX6 for stimulation) and 100 μL of complete media (total volume=2004). ELISpot plates were incubated for 18 hours at 37° C., 5% $CO_2$ in a humidified environment.

Three doses of the FP-01.1 were adjusted by volume maintaining a constant FCP concentration of 500 μg/ml per peptide. SD rats were injected IM with 12.5, 50 or 100 μg/peptide of FP-01.1 on days 0 and 14 and their spleens harvested on day 24 for IFN-γ ELISPOT analysis after 18 hours incubation with individual native peptides from FP-01.1. Both 12.5 μg/peptide and 50 μg/peptide doses were injected at a single site in a volume of 250 and 100 μl respectively, while the 100 μg/peptide dose was injected in 2×1000 volumes at two different sites.

Figure 17:
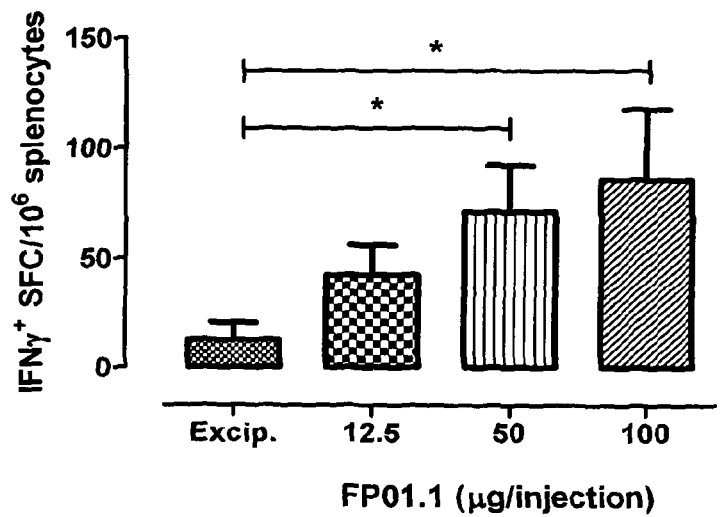
FIG. 17 shows the volume adjusted dose response in rats. FP-01.1 induced a positive IFN-γ T cell response at all dose levels tested in a dose dependent fashion.

FP-01.1 induced a positive IFN-γ T cell response at all dose levels tested in a dose dependent fashion (FIG. 17).

Example 15

Clinical Trial Data for FP01.1

Three ascending doses of FP-01.1 (50, 150, 500 μg/peptide) and placebo given on days 1, 29 was assessed for safety, tolerability and immunogenicity in a phase I clinical trial in a total 48 healthy individuals.

FP-01.1 was well tolerated by all three cohorts, following two intramuscular injections. There was no clear evidence of a dose-dependent relationship in the incidence of TEAEs, laboratory parameters or injection site reactions. No subject exhibited any marked local or systemic reaction to vaccination on either the first or second exposure in any of the three cohorts.

Vaccine-induced T cell responses were assessed using an ex vivo IFN-γ ELISpot assay. PBMCs were stimulated with 6 individual peptides (corresponding to peptides contained in the vaccine) for 18 hours. Positive assay responses were defined as the mean of number of spots in the negative control wells +2 standard deviations of the mean. The number of spots for each of the 6 peptides was cumulated to obtain the "sum for long peptides" and expressed as a number of spots per million input PBMCs.

Figure 18:
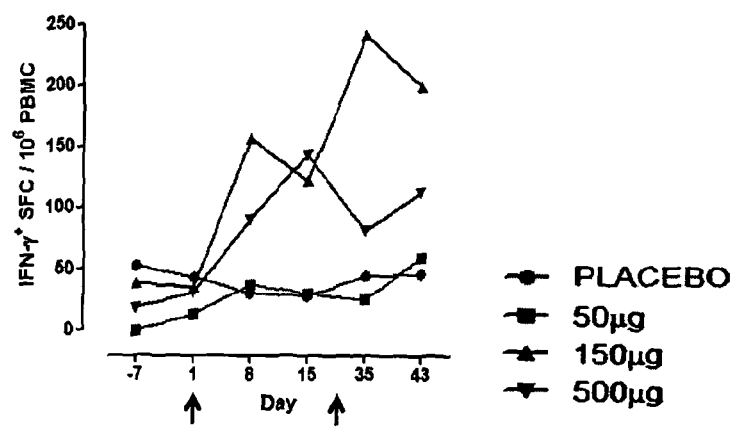
FIG. 18 shows vaccine-induced T cell responses observed using an ex vivo IFN-γ ELISpot assay. PBMCs were stimulated with 6 individual peptides (corresponding to peptides contained in the vaccine) for 18 hours. Positive assay responses were defined as the mean of number of spots in the negative control wells +2 standard deviations of the mean. The number of spots for each of the 6 peptides was cumulated to obtain the "sum for long peptides" and expressed as a number of spots per million input PBMCs.

FP-01.1 was demonstrated to be immunogenic. 150 μg FP-01.1 dose group shows a higher response compared with the two other vaccine doses and the placebo group as observed in FIG. 18. In this dose group, a booster effect is observed after the second injection supporting the concept of booster amplification with multiple injections for peptide vaccines.

SEQUENCE LISTING

<160> NUMBER OF SEQ ID NOS: 28

<210> SEQ ID NO 1
<211> LENGTH: 35
<212> TYPE: PRT
<213> ORGANISM: Influenza virus

<400> SEQUENCE: 1

His Met Ala Ile Ile Lys Lys Tyr Thr Ser Gly Arg Gln Glu Lys Asn
1 5 10 15

Pro Ser Leu Arg Met Lys Trp Met Met Ala Met Lys Tyr Pro Ile Thr
20 25 30

Ala Asp Lys
35

<210> SEQ ID NO 2
<211> LENGTH: 35
<212> TYPE: PRT
<213> ORGANISM: Influenza virus

<400> SEQUENCE: 2

Val Ala Tyr Met Leu Glu Arg Glu Leu Val Arg Lys Thr Arg Phe Leu
1 5 10 15

Pro Val Ala Gly Gly Thr Ser Ser Val Tyr Ile Glu Val Leu His Leu
20 25 30

Thr Gln Gly
35

<210> SEQ ID NO 3
<211> LENGTH: 35
<212> TYPE: PRT
<213> ORGANISM: Influenza virus

<400> SEQUENCE: 3

Tyr Ile Thr Arg Asn Gln Pro Glu Trp Phe Arg Asn Val Leu Ser Ile
1 5 10 15

Ala Pro Ile Met Phe Ser Asn Lys Met Ala Arg Leu Gly Lys Gly Tyr
20 25 30

Met Phe Glu
35

<210> SEQ ID NO 4
<211> LENGTH: 35
<212> TYPE: PRT
<213> ORGANISM: Influenza virus

<400> SEQUENCE: 4

Ala Pro Ile Met Phe Ser Asn Lys Met Ala Arg Leu Gly Lys Gly Tyr
1 5 10 15

Met Phe Glu Ser Lys Arg Met Lys Leu Arg Thr Gln Ile Pro Ala Glu
20 25 30

Met Leu Ala
35

<210> SEQ ID NO 5
<211> LENGTH: 35
<212> TYPE: PRT
<213> ORGANISM: Influenza virus

<400> SEQUENCE: 5

-continued

Asp Gln Val Arg Glu Ser Arg Asn Pro Gly Asn Ala Glu Ile Glu Asp
1               5                   10                  15

Leu Ile Phe Leu Ala Arg Ser Ala Leu Ile Leu Arg Gly Ser Val Ala
            20                  25                  30

His Lys Ser
        35

<210> SEQ ID NO 6
<211> LENGTH: 35
<212> TYPE: PRT
<213> ORGANISM: Influenza virus

<400> SEQUENCE: 6

Asp Leu Glu Ala Leu Met Glu Trp Leu Lys Thr Arg Pro Ile Leu Ser
1               5                   10                  15

Pro Leu Thr Lys Gly Ile Leu Gly Phe Val Phe Thr Leu Thr Val Pro
            20                  25                  30

Ser Glu Arg
        35

<210> SEQ ID NO 7
<211> LENGTH: 35
<212> TYPE: PRT
<213> ORGANISM: Influenza virus

<400> SEQUENCE: 7

His Met Ala Ile Ile Lys Lys Tyr Thr Ser Gly Arg Gln Glu Lys Asn
1               5                   10                  15

Pro Ala Leu Arg Met Lys Trp Met Met Ala Met Lys Tyr Pro Ile Thr
            20                  25                  30

Ala Asp Lys
        35

<210> SEQ ID NO 8
<211> LENGTH: 35
<212> TYPE: PRT
<213> ORGANISM: Influenza virus

<400> SEQUENCE: 8

Val Ala Tyr Met Leu Glu Arg Glu Leu Val Arg Lys Thr Arg Phe Leu
1               5                   10                  15

Pro Val Ala Gly Gly Thr Ser Ser Ile Tyr Ile Glu Val Leu His Leu
            20                  25                  30

Thr Gln Gly
        35

<210> SEQ ID NO 9
<211> LENGTH: 35
<212> TYPE: PRT
<213> ORGANISM: Influenza virus

<400> SEQUENCE: 9

Val Ala Tyr Met Leu Glu Arg Glu Leu Val Arg Lys Thr Arg Phe Leu
1               5                   10                  15

Pro Val Ser Gly Gly Thr Ser Ser Val Tyr Ile Glu Val Leu His Leu
            20                  25                  30

Thr Gln Gly
        35

<210> SEQ ID NO 10

```
<211> LENGTH: 35
<212> TYPE: PRT
<213> ORGANISM: Influenza virus

<400> SEQUENCE: 10

Tyr Ile Thr Lys Asn Gln Pro Glu Trp Phe Arg Asn Ile Leu Ser Ile
1               5                   10                  15

Ala Pro Ile Met Phe Ser Asn Lys Met Ala Arg Leu Gly Lys Gly Tyr
            20                  25                  30

Met Phe Glu
        35

<210> SEQ ID NO 11
<211> LENGTH: 35
<212> TYPE: PRT
<213> ORGANISM: Influenza virus

<400> SEQUENCE: 11

Ala Pro Ile Met Phe Ser Asn Lys Met Ala Arg Leu Gly Lys Gly Tyr
1               5                   10                  15

Met Phe Glu Ser Lys Ser Met Lys Leu Arg Thr Gln Ile Pro Ala Glu
            20                  25                  30

Met Leu Ala
        35

<210> SEQ ID NO 12
<211> LENGTH: 35
<212> TYPE: PRT
<213> ORGANISM: Influenza virus

<400> SEQUENCE: 12

Asp Gln Val Arg Glu Ser Arg Asn Pro Gly Asn Ala Glu Ile Glu Asp
1               5                   10                  15

Leu Thr Phe Leu Ala Arg Ser Ala Leu Ile Leu Arg Gly Ser Val Ala
            20                  25                  30

His Lys Ser
        35

<210> SEQ ID NO 13
<211> LENGTH: 33
<212> TYPE: PRT
<213> ORGANISM: Influenza virus

<400> SEQUENCE: 13

Ser Pro Gly Met Met Met Gly Met Phe Asn Met Leu Ser Thr Val Leu
1               5                   10                  15

Gly Val Ser Ile Leu Asn Leu Gly Gln Lys Lys Tyr Thr Lys Thr Thr
            20                  25                  30

Tyr

<210> SEQ ID NO 14
<211> LENGTH: 35
<212> TYPE: PRT
<213> ORGANISM: Influenza virus

<400> SEQUENCE: 14

Lys Lys Lys Ser Tyr Ile Asn Lys Thr Gly Thr Phe Glu Phe Thr Ser
1               5                   10                  15

Phe Phe Tyr Arg Tyr Gly Phe Val Ala Asn Phe Ser Met Glu Leu Pro
            20                  25                  30
```

Ser Phe Gly
        35

<210> SEQ ID NO 15
<211> LENGTH: 33
<212> TYPE: PRT
<213> ORGANISM: Influenza virus

<400> SEQUENCE: 15

Gln Ser Arg Met Gln Phe Ser Ser Leu Thr Val Asn Val Arg Gly Ser
1               5                   10                  15

Gly Met Arg Ile Leu Val Arg Gly Asn Ser Pro Val Phe Asn Tyr Asn
            20                  25                  30

Lys

<210> SEQ ID NO 16
<211> LENGTH: 35
<212> TYPE: PRT
<213> ORGANISM: Influenza virus

<400> SEQUENCE: 16

Pro Asp Leu Tyr Asp Tyr Lys Glu Asn Arg Phe Ile Glu Ile Gly Val
1               5                   10                  15

Thr Arg Arg Glu Val His Ile Tyr Tyr Leu Glu Lys Ala Asn Lys Ile
            20                  25                  30

Lys Ser Glu
        35

<210> SEQ ID NO 17
<211> LENGTH: 36
<212> TYPE: PRT
<213> ORGANISM: Influenza virus

<400> SEQUENCE: 17

Lys His Met Ala Ile Ile Lys Lys Tyr Thr Ser Gly Arg Gln Glu Lys
1               5                   10                  15

Asn Pro Ser Leu Arg Met Lys Trp Met Met Ala Met Lys Tyr Pro Ile
            20                  25                  30

Thr Ala Asp Lys
        35

<210> SEQ ID NO 18
<211> LENGTH: 36
<212> TYPE: PRT
<213> ORGANISM: Influenza virus

<400> SEQUENCE: 18

Lys Val Ala Tyr Met Leu Glu Arg Glu Leu Val Arg Lys Thr Arg Phe
1               5                   10                  15

Leu Pro Val Ala Gly Gly Thr Ser Ser Val Tyr Ile Glu Val Leu His
            20                  25                  30

Leu Thr Gln Gly
        35

<210> SEQ ID NO 19
<211> LENGTH: 36
<212> TYPE: PRT
<213> ORGANISM: Influenza virus

<400> SEQUENCE: 19

```
Lys Tyr Ile Thr Arg Asn Gln Pro Glu Trp Phe Arg Asn Val Leu Ser
1               5                   10                  15

Ile Ala Pro Ile Met Phe Ser Asn Lys Met Ala Arg Leu Gly Lys Gly
                20                  25                  30

Tyr Met Phe Glu
            35

<210> SEQ ID NO 20
<211> LENGTH: 36
<212> TYPE: PRT
<213> ORGANISM: Influenza virus

<400> SEQUENCE: 20

Lys Ala Pro Ile Met Phe Ser Asn Lys Met Ala Arg Leu Gly Lys Gly
1               5                   10                  15

Tyr Met Phe Glu Ser Lys Arg Met Lys Leu Arg Thr Gln Ile Pro Ala
                20                  25                  30

Glu Met Leu Ala
            35

<210> SEQ ID NO 21
<211> LENGTH: 36
<212> TYPE: PRT
<213> ORGANISM: Influenza virus

<400> SEQUENC

<212> TYPE: PRT
<213> ORGANISM: Influenza virus

<400> SEQUENCE: 24

Lys Ser Pro Gly Met Met Gly Met Phe Asn Met Leu Ser Thr Val
1               5                   10                  15

Leu Gly Val Ser Ile Leu Asn Leu Gly Gln Lys Lys Tyr Thr Lys Thr
            20                  25                  30

Thr Tyr

<210> SEQ ID NO 25
<211> LENGTH: 36
<212> TYPE: PRT
<213> ORGANISM: Influenza virus

<400> SEQUENCE: 25

Lys Lys Lys Lys Ser Tyr Ile Asn Lys Thr Gly Thr Phe Glu Phe Thr
1               5                   10                  15

Ser Phe Phe Tyr Arg Tyr Gly Phe Val Ala Asn Phe Ser Met Glu Leu
            20                  25                  30

Pro Ser Phe Gly
            35

<210> SEQ ID NO 26
<211> LENGTH: 36
<212> TYPE: PRT
<213> ORGANISM: Influenza virus

<400> SEQUENCE: 26

Lys Tyr Ile Thr Lys Asn Gln Pro Glu Trp Phe Arg Asn Ile Leu Ser
1               5                   10                  15

Ile Ala Pro Ile Met Phe Ser Asn Lys Met Ala Arg Leu Gly Lys Gly
            20                  25                  30

Tyr Met Phe Glu
            35

<210> SEQ ID NO 27
<211> LENGTH: 34
<212> TYPE: PRT
<213> ORGANISM: Influenza virus

<400> SEQUENCE: 27

Lys Gln Ser Arg Met Gln Phe Ser Ser Leu Thr Val Asn Val Arg Gly
1               5                   10                  15

Ser Gly Met Arg Ile Leu Val Arg Gly Asn Ser Pro Val Phe Asn Tyr
            20                  25                  30

Asn Lys

<210> SEQ ID NO 28
<211> LENGTH: 36
<212> TYPE: PRT
<213> ORGANISM: Influenza virus

<400> SEQUENCE: 28

Lys Pro Asp Leu Tyr Asp Tyr Lys Glu Asn Arg Phe Ile Glu Ile Gly
1               5                   10                  15

Val Thr Arg Arg Glu Val His Ile Tyr Tyr Leu Glu Lys Ala Asn Lys
            20                  25                  30

Ile Lys Ser Glu
            35

The invention claimed is:

1. An aqueous acidic formulation for use in the preparation of a pharmaceutically acceptable fluorocarbon-linked peptide formulation, the aqueous acidic formulation comprising a first fluorocarbon-linked peptide, wherein:
   the peptide linked to the fluorocarbon is 20 to 50 amino acid residues long, comprises at least 50% hydrophobic amino acid residues and has an isoelectric point greater than or equal to 7, but does not comprise a contiguous sequence of 20 amino acid residues comprising more than 80% hydrophobic amino acid residues; and
   (ii) the fluorocarbon-linked peptide is present in micelles.

2. The aqueous acidic formulation according to claim 1, further comprising acetic acid.

3. The aqueous acidic formulation according to claim 1, further comprising one or more fluorocarbon-linked peptides that:
   (i) are 20 to 50 amino acid residues long;
   (ii) comprise at least 50% hydrophobic amino acid residues; and/or
   (iii) have an isoelectric point greater than or equal to 7; and/or
the first fluorocarbon-linked peptide and/or one or more of the further fluorocarbon-linked peptides comprises a peptide that:
   (iv) comprises a positively charged amino acid in the last 15 contiguous amino acids distal to the fluorocarbon; and/or
   (v) does not comprise a contiguous sequence of 20 amino acid residues comprising more than 80% hydrophobic amino acid residues.

4. A The aqueous acidic formulation according to claim 1, wherein the formulation does not comprise a fluorocarbon-linked peptide in which the peptide linked to the fluorocarbon:
   (i) has an isoelectric point of less than 7; and/or
   (ii) does not comprise a positively charged amino acid in the last 15 contiguous amino acids distal to the fluorocarbon.

5. A The aqueous acidic formulation according to claim 1, wherein the peptide linked to the fluorocarbon is an immunogenic peptide derived from a pathogen, autologous protein or tumor cell.

6. A method for obtaining a pharmaceutically acceptable fluorocarbon-linked peptide formulation, said method comprising:
   (i) solubilising a fluorocarbon-linked peptide in acetic acid;
   (ii) filter-sterilising the solubilised fluorocarbon-linked peptide; and
   (iii) drying the filter-sterilised fluorocarbon-linked peptide.

7. The method according to claim 6, wherein the peptide linked to the fluorocarbon is at least 20 amino acid residues long and comprises at least 50% hydrophobic amino acid residues and has an isoelectric point greater than or equal to 7.

8. The method according to claim 6, wherein:
   (i) a mixture of the fluorocarbon-linked peptide and one or more further fluorocarbon-linked peptides are solubilised in acetic acid; and/or
   (ii) the method further comprises blending the solubilised fluorocarbon-linked peptide with one or more further solubilised fluorocarbon-linked peptides.

9. The method according to claim 6, wherein the peptide linked to the fluorocarbon is an immunogenic peptide derived from a pathogen, autologous protein or tumor cell.

10. The aqueous acidic formulation according to claim 1, wherein the formulation has a pH of 5 or less.

11. The aqueous acidic formulation according to claim 1 further comprising one or more additional fluorocarbon-linked peptides present in micelles with a diameter of less than 0.22 μm.

12. The aqueous acidic formulation according to claim 1, wherein at least 80% of the fluorocarbon-linked peptide micelles have a diameter of less than 100 nm.

13. The aqueous acidic formulation according to claim 1, wherein the aqueous acidic formulation comprises six fluorocarbon-linked peptides, wherein each of the peptides have the sequences set out in SEQ ID NOs: 1 to 6 and wherein the aqueous acidic formulation comprises no other fluorocarbon-linked peptides.

* * * * *